United States Patent [19]

Bush et al.

[11] Patent Number: 5,462,963
[45] Date of Patent: Oct. 31, 1995

[54] CHELATOR COMPOSITIONS COMPRISING α-DIAMINE COMPOUNDS

[75] Inventors: Rodney D. Bush, Fairfield; Donald L. Bissett, Hamilton, both of Ohio

[73] Assignee: The Procter & Gamble Company, Cincinnati, Ohio

[21] Appl. No.: 739,933

[22] Filed: Aug. 2, 1991

Related U.S. Application Data

[63] Continuation-in-part of Ser. No. 514,892, Apr. 26, 1990, abandoned.

[51] Int. Cl.$^6$ ............ A61K 31/34; A61K 31/38; A61K 31/40; A61K 31/15
[52] U.S. Cl. ............ 514/248; 514/249; 514/252; 514/266; 514/269; 514/308; 514/364; 514/378; 514/381; 514/397; 514/406; 514/438; 514/444; 514/471; 514/640; 544/237; 544/238; 544/264; 544/296; 544/353; 544/357; 546/140; 548/125; 548/247; 548/252; 548/314.4; 548/365.4; 548/518; 549/59; 549/60; 549/472; 549/492; 564/253; 564/256; 564/265
[58] Field of Search ............ 544/237, 238, 544/264, 296, 353, 357; 546/140; 548/125, 247, 252, 314.4, 365.4, 518; 549/59, 60, 472, 492; 564/253, 256, 265; 514/248, 249, 252, 266, 269, 308, 364, 378, 381, 397, 406, 422, 444, 438, 471, 640

[56] References Cited

U.S. PATENT DOCUMENTS

| | | | |
|---|---|---|---|
| 3,483,231 | 9/1969 | Marcus | 260/396 |
| 3,836,528 | 9/1974 | Minami et al. | 260/240 A |
| 4,401,649 | 8/1983 | Green | 424/60 |
| 4,678,810 | 7/1987 | Danrée | 514/640 |
| 4,902,719 | 2/1990 | Gerhart et al. | 514/564 |
| 5,026,875 | 6/1991 | Takeda et al. | 549/201 |
| 5,069,900 | 12/1991 | Linder | 424/1.1 |

FOREIGN PATENT DOCUMENTS

| | | |
|---|---|---|
| 0313305 | 4/1989 | European Pat. Off. . |
| 1-135887 | 5/1989 | Japan . |

OTHER PUBLICATIONS

Grundmann, C., H.–D. Frommeld, K. Flory & S. K. Datta, "Nitril Oxides. XI. Dimerization of a Sterically Hindered Nitrile Oxide. Dimesitylfurazan Oxide", *The Journal of Organic Chemistry*, vol. 33, No. 4 (1988), pp. 1464–1466.

Keller, H. J. & R. Lehmann, "Planare Komplexe von unsymmetrisch substituierten Alkyl–und Aryl–α,β–diondioximen mit den Ionen Nickel(II), Palladium(II) und Platin(II)", *Zeitschrift Fur Naturforschung*, vol. 34B, No. 2 (1979), pp. 245–250 (translation attached).

Toul, J., J. Padrta & A. Okac, "Thin Layer and Paper Chromatography of Some 1,2–Dioximes and Their Monoximes", *Journal of Chromatography*, vol. 57, No. 1 (1971), pp. 107–119.

Merck Index, Merck & Co., Rahway, New Jersey; 1989, p. 674.

Cross, C. E., B. Halliwell, E. T. Borish, W. A. Pryor, B. N. Ames, R. L. Saul, J. M. McCord & D. Harman, "Oxygen Radicals and Human Disease", Annals of Internal Medicine, vol. 107 (1987), pp. 526–545.

Davies, K. J. A., "Protein Damage and Degradation by Oxygen Radicals", The Journal of Biological Chemistry, vol. 262 (1987), pp. 9895–9901.

Black, H. S., "Potential Involvement of Free Radical Reactions in Ultraviolet Light–Mediated Cutaneous Damage", Photochemistry and Photobiology, vol. 46 (1987), pp. 213–221.

Braughler, J. M., J. A. Duncan & R. L. Chase, "The Involvement of Iron in Lipid Peroxidation", The Journal of Biological Chemistry, vol. 261 (1986), pp. 10282–10289.

de Mello Filho, A. C. & R. Meneghini, "Protection of Mammalian Cells by o–Phenanthroline from Lethal DNA–damaging Effects Produced by Active Oxygen Species", Biochemica et Biophysica Acta, vol. 847 (1985), pp. 82–89.

Nunez, M. T., E. S. Cole & J. Glass, "The Reticulocyte Plasma Membrane Pathway of Iron Uptake as Determined (List continued on next page.)

Primary Examiner—Richard L. Raymond
Attorney, Agent, or Firm—Milton B. Graff; Jerry J. Yetter; John M. Howell

[57] ABSTRACT

The present invention involves photoprotective compositions which are useful for topical application to prevent damage to skin caused by acute or chronic exposure to ultraviolet light comprising chelating agents having the structure:

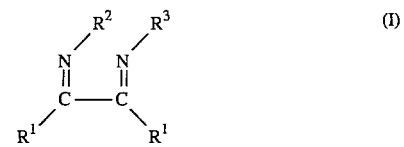

wherein each —$R^1$ is independently selected from the group consisting of alkyl, aryl, heteroaryl and heterocycle, or the —$R^1$'s are covalently bonded together to form a cyclic alkyl or heterocyclic ring; —$R^2$ and —$R^3$ are —$OR^4$, in which case there is no bond or a polar bond between —$R^2$ and the nitrogen covalently bonded to —$R^3$, each —$R^4$ being independently selected from the group consisting of hydrogen, alkyl and aryl, except that both —$R^4$'s are not methyl when both —$R^1$'s are furyl; or —$R^2$ is —O— and is covalently bonded to the nitrogen which is covalently bonded to —$R^3$, and —$R^3$ is —O— (there being a + charge on the nitrogen to which it is bonded) or nil;

wherein the α-diamine compounds consist essentially of compounds wherein =$NR^2$ and =$NR^3$ are in amphi configuration when both —$R^2$ and —$R^3$ are —OH, and when both —$R^1$'s are furyl or the —$R^1$'s are covalently bonded together to form a cyclohexanedione structure.

Methods for using such compositions to prevent damage to skin caused by acute or chronic exposure to ultraviolet light are also involved.

16 Claims, No Drawings

OTHER PUBLICATIONS by the Mechanism of α,α'–Dipyridyl Inhibition", The Journal of Biological Chemistry, vol. 258 (1983), pp. 1146–1151.

Morgan, E. H., "Chelator–mediated Iron Efflux from Reticulocytes", Biochemica et Biophysica Acta, vol. 733 (1983), pp. 39–50.

Martell, A. E., "The Design and Synthesis of Chelating Agents", Development of Iron Chelators for Clinical Use, Martell, Anderson & Badman, eds., Elsevier North Holland, Inc., New York, N.Y. (1981), pp. 67–104.

CHELATOR COMPOSITIONS COMPRISING α-DIAMINE COMPOUNDS

This is a continuation-in-part of application Ser. No. 514,892, filed on Apr. 25, 1990, now abandoned.

TECHNICAL FIELD

This invention relates to pharmaceutical compositions useful for regulating biochemical and cellular damage resulting from free radical reactions in living persons.

This invention further relates to topical compositions useful for protecting the skin from the harmful effects of ultraviolet irradiation, such as sunburn and sun-induced premature aging of the skin.

BACKGROUND OF THE INVENTION

The damaging effects of sunlight on skin are well documented. Much damage is due to routine day-to-day activities in the sunlight.

The major short term hazard of prolonged exposure to sunlight is erythema (i.e., sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema.

In addition to the short term hazard of erythema, there are also long term hazards associated with UV radiation exposure. One of these long term hazards is malignant changes in the skin surface. Numerous epidemiologic studies demonstrate a strong relationship between sunlight exposure and human skin cancer. Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed, Chapter 26, pp. 499–511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 4, pp. 15–24 (1982); and U.S. Pat. No. 4,387,089, DePolo, issued Jun. 7, 1983. Hence, although the immediate effects of ultraviolet radiation may be cosmetically and socially gratifying, the long-term hazards are cumulative and potentially serious.

Sunblock agents are commercially available to protect the skin from UV radiation. These agents scatter or reflect ultraviolet radiation. Examples include titanium dioxide and zinc oxide. However, these agents are very susceptible to rub-off or wear-off resulting in little or no protection.

The most common agents for sun protection are sunscreens. These agents exert their effects through absorption of ultraviolet radiation so that it cannot penetrate the skin. Sunscreens must remain on the surface of the skin during exposure. However, sunscreens are easily rubbed off or washed off by sweating or swimming and can also be lost by penetration into the skin.

Conjugated dienoic acids and their derivatives, in general, are known to be useful as quenchers for protecting the skin from harmful effects of UV exposure. For example, the use of a number of compounds, including 2,4-hexadien-1-ol, for controlling the chronic effects of prolonged exposure to sunlight is disclosed in U.S. Pat. No. 4,098,881, Majeti, issued Jul. 4, 1978. The use of sorbic acid or salts thereof in sunscreen formulations is also known. See e.g., U.S. Pat. No. 4,264,581, Kerkhof et al., issued Apr. 28, 1981.

Tocopherol (Vitamin E) and its esters have been disclosed for use as a photoprotector in topical compositions, without interfering with the tanning response. See, e.g., U.S. Pat. No. 4,144,325, Voyt, issued Mar. 13, 1974; U.S. Pat. No. 4,248,861, Schutt, issued Feb. 3, 1981; U.S. Pat. No. 4,000,276, Hasunuma et al., issued Dec. 28, 1976; U.S. Pat. No. 4,847,071, Bissett, Bush, and Chatterjee, issued Jul. 11, 1989; and European Patent Application 166,221, Tuominen, published Jan. 2, 1986.

Hart, *Cosmetics and Toiletries*, 93(12), 28–30 (1978), discloses the utilization of low levels of chelating agents such as ethylenediaminetetraacetic acid (EDTA) in cosmetic formulations as preservatives. Particularly disclosed is the use of EDTA in sunscreen lotions and creams to prevent dark color formation from the reaction of p-aminobenzoic acid derivatives with iron. See also, Hart, *Cosmetics and Toiletries*, 98(4), 54–58 (1983). Japanese Patent Application 61-215,314 discloses a topical composition for protecting skin from UV-rays containing EDTA or a phosphoric acid or salt, 4-(1,1-dimethylethyl)-4'-methoxydibenzoylmethane and inorganic powders. The acids and their salts are added as preservatives. See also Japanese Patent Application 61-215,313, published Sep. 25, 1986, and U.S. Pat. No. 4,579,844, Rovee, issued Apr. 1, 1986. Wooley, et al., *Biochem. J.*, 169, 265–276 (1978), discloses the inhibition of skin collagenase utilizing EDTA, 1,10-phenanthroline, cysteine, dithiothreitol, or sodium aurothiemaleate.

It is well-known that ultraviolet light induces inflammation of the skin and harmful photochemical reactions therein. During exposure and as repair of the UV damage takes place, super-oxide ($O_2^-$) radicals are formed in the skin. UV irradiation also causes some microvascular damage in the skin. (See Kligman et al., *Photoderm.*, 3, 215–227 (1986)). This leads to local hemorrhage and "leakage" of blood cells into the dermis. Iron from the hemoglobin accumulates in the extra-cellular matrix of the tissue as $Fe^{+2}$ and $Fe^{+3}$. It is known that iron catalytically participates in the conversion of superoxide radicals to hydroxyl radicals, a species which is known to be very damaging to tissue. (See Davies, *J. Biol. Chem.*, Vol. 262, No 20 (1987), pp. 9895–9901.) Another process which is damaging to tissue is membrane lipid peroxidation, which is also accelerated by iron. (See Halliwell and Gutteridge, *Free Radicals in Biology and Medicine*, Claredon Press, Oxford, England (1985), p. 147.)

In addition to their role in UV radiation induced tissue damage, oxygen radicals are known to be capable of reversibly or irreversibly damaging compounds of all biochemical classes, including nucleic acids, proteins and free amino acids, lipids and lipoproteins, carbohydrates, and connective tissue macromolecules. These compounds may have an impact on such cell activities as membrane function, metabolism, and gene expression. (See C. E. Cross, G. Halliwell, E. T. Borish, W. A. Pryor, B. N. Ames, R. L. Saul, J. M. McCord, and D. Harman, "Oxygen Radicals and Human Disease", *Annals of Internal Medicine* 107(4), 526–545 (1987).) Clinical conditions in which oxygen radicals are thought to be involved include those concerning multiorgan involvement, including inflammatory-immune injury such as glomerulonephritis (idiopathic, membranous), vasculitis (hepatitis B virus, drugs), autoimmune disease; ischemia-reflow states; drug and toxin-induced reactions; iron overload such as idiopathic hemochromatosis, dietary iron overload (red wine, beer brewed in iron pots), thalassemia and other chronic anemias; nutritional deficiencies, such as Kwashiorkor, vitamin E deficiency; alcohol; radiation injury; aging, such as disorders of "premature aging", immune deficiency of age; cancer and amyloid diseases. Additional conditions in which oxygen radicals are thought to be involved include those concerning primary single organ involvement including erythrocyte related conditions, such as phenylhydrazine, primaquine, lead poisoning, protoporphyrin photo-oxidation, malaria, sickle-cell anemia, favism, Fanconi anemia; lung related conditions such as cigarette-smoking effects, emphysema, hyperoxia, bronchopulmonary dysplasia, oxidant pollutants, acute respiratory distress syndrome, mineral dust pneumoconiosis, bleomycin toxicity, paraquat toxicity; heart and cardiovascular system related conditions, such as alcohol cardiomyopathy, Keshan disease (selenium deficiency), atherosclerosis, doxorubicin toxicity; kidney related conditions, such as nephrotic antiglomerular basement membrane disease, aminoglycoside nephrotoxicity, heavy metal nephrotoxicity, renal graft rejection; gastrointestinal tract related conditions, such as endotoxin liver injury, carbon tetrachloride liver injury, diabetogenic action of alloxan, free-fatty-acid-induced pancreatitis, nonsteroidal-anti-inflammatory-drug induced lesions; joint abnormalities, such as rheumatoid arthritis; brain related conditions, such as hyperbaric oxygen, neurotoxins, senile dementia, Parkinson disease-MPTP, hypertensive cerebrovascular injury, cerebral trauma, neuronal ceroid lipofuscinoses, allergic encephalomyelitis and other demyelinating diseases, ataxia-telangiectasia syndrome, potentiation of traumatic injury, aluminum overload, a-beta-lipoproteinemia; eye related conditions, such as cataractogenesis, ocular hemorrhage, degenerative retinal damage, retinopathy of prematurity, photic retinopathy and skin related conditions, such as solar radiation, thermal injury, porphyria, contact dermatitis, photosensitive dyes, and bloom syndrome. (See *Cross, et. al.,* 1987.)

Black, *Photochem. Photobiol.,* 46(2), 213–221 (1987), speculates, based on circumstantial evidence, that free radicals may cause at least some UV-induced skin damage. The effect of systemically or intraperitoneally administered antioxidants on peroxide formation is discussed.

Braughler, et al., *J. Biol. Chem.,* 261(22), 10282–10289 (1986), discusses iron-initiated lipid peroxidation reactions in the context of brain synoptosomes. It is shown that the use of a chelator, EDTA, will prevent the reactions from starting.

Nunez et al., *J. Biol. Chem.,* 258(2), 1146–1151 (1983), discusses the cellular mechanism by which iron is released by reticulocytes. It was found that iron (II) chelators (e.g., phenanthroline, dipyridyl), but not iron (III) chelators, were useful in the study of this mechanism.

deMello Filho, et al., *Biochem. et Biophys. Acta,* 847, 82–89 (1985), describes cell culture work which suggests that the inhibition of the iron-initiated peroxidation reaction by phenanthroline may prevent cellular damage caused by inflammation.

Morgan, *Biochem. Biophys. Acta,* 733(1), 39–50 (1983), discusses the mechanism by which certain iron chelators inhibit cellular iron uptake after release from transfertin while it is still in the membrane fraction of the cells.

European Patent Application 0 313 305, Bissett, Bush, and Chatterjee, published Apr. 26, 1989, discloses photoprotection compositions comprising various chelating agents, including 2-furildioxime.

It is an object of the present invention to provide a pharmaceutical composition, the use of which will regulate biochemical damage resulting from free radical reactions in living persons.

It is also an object of the present invention to provide a method for regulating biochemical damage resulting from free radical reactions in living persons.

It is also an object of the present invention to provide a topical composition in a stable form, the use of which will prevent chronic (photoaging) effects of exposure to the sun.

It is also an object of the present invention to provide a topical composition for preventing the deleterious effects of the sun with minimal interference to the tanning response.

It is also an object of the present invention to provide a cleansing composition for preventing the deleterious effects of the sun with minimal interference to the tanning response.

It is also an object of the present invention to provide a method for preventing the deleterious effects of the sun with minimal interference to the tanning response.

It is further an object of the present invention to provide a photoprotection composition which penetrates into the skin and which has low susceptiblility to rub-off, wear-off or wash-off.

It is a still further object of the present invention to provide a photoprotection composition which can be applied to the skin in advance of UV exposure without significant loss of efficacy.

SUMMARY OF THE INVENTION

The present invention relates to a pharmaceutical composition comprising a safe and effective amount of one or more α-diamine compounds having the structure:

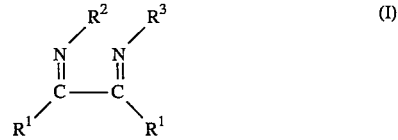

wherein each —$R^1$ is independently selected from the group consisting of alkyl, aryl, heteroaryl and heterocyclic, or the —$R^1$'s are covalently bonded together to form a cyclic alkyl or heterocyclic ring; —$R^2$ and —$R^3$ are —$OR^4$, in which case there is no bond or a polar bond between —$R^2$ and the nitrogen covalently bonded to —$R^3$, each —$R^4$ being independently selected from the group consisting of hydrogen, alkyl and aryl, except that both —$R^4$'s are not methyl when both —$R^1$'s are furyl; or —$R^2$ is —O— and is covalently bonded to the nitrogen which is covalently bonded to —$R^3$, and —$R^3$ is —O— there being a + charge on the nitrogen to which it is bonded) or nil; wherein the α-diamine compounds consist essentially of compounds wherein =$NR^2$ and =$NR^3$ are in amphi configuration when both —$R^2$ and —$R^3$ are —OH, and when both —$R^1$'s are furyl or the —$R^1$'s are covalently bonded together to form a cyclohexanedione structure.

The present invention also relates to a composition useful for topical application comprising a safe and photoprotectively effective amount of a chelating agent having structure (I) in combination with a topical carrier.

The present invention further relates to methods of regulating the deleterious effects of free radical reactions in living tissue including the deleterious effects of ultraviolet exposure to the skin.

DETAILED DESCRIPTION OF THE INVENTION

As used herein, "amphi", "amphi form", and "amphi position" refer to the positioning of the —$R^2$ and —$R^3$ groups of the present invention relative to one another such that the —$R^2$ and —$R^3$ groups point in the same direction as opposed to anti or syn forms wherein the —$R^2$ and —$R^3$ groups point in opposite directions away from or toward each other, respectively.

As used herein, "alkyl" means carbon-containing chains which may be straight, branched, or cyclic; substituted or unsubstituted; and which may be saturated, monounsaturated (i.e., one double or triple bond in the chain), or polyunsaturated (i.e., two or more double bonds in the chain; two or more triple bonds in the chain; one or more double and one or more triple bonds in the chain). Unless otherwise indicated, alkyl are preferably as follows. Preferred alkyl are straight or branched chain, more preferably straight chain. Preferred alkyl are unsubstituted. Preferred alkyl are saturated or monounsaturated, more preferably saturated. As used herein, "alkanyl" means a saturated alkyl group. Preferred alkyl are $C_1$–$C_{20}$, more preferably $C_1$–$C_{18}$, more preferably still $C_1$–$C_{12}$, more preferably $C_1$–$C_6$, more preferably $C_1$–$C_2$, most preferably $C_1$.

As used herein, "aryl" and "heteroaryl" mean aryl or heteroaryl rings which may be substituted or unsubstituted, preferably mono-, di-, or tri-substituted or unsubstituted, more preferably mono-substituted or unsubstituted, most preferably unsubstituted. Preferred heteroaryl rings comprise at least one oxygen, nitrogen, or sulfur atom in the ring structure. Preferred aryls are phenyl, naphthyl and hydroxyphenyl, especially phenyl. Preferred heteroaryl s include furyl, thienyl, pyrrolyl, imidazolyl, pyrazolyl, pyrazinyl, pyrimidinyl, pyridazinyl, isoquinolyl, purinyl, phthalazinyl, quinoxalinyl, furazanyl, isoxazolyl, and tetrazolyl; more preferred are furyl, thienyl and pyrrolyl, especially furyl.

As used herein, "heterocyclic" means cyclic rings having at least one ring atom that is other than carbon, preferably nitrogen, oxygen or sulfur. Heterocyclic rings may be unsaturated, but are not aromatic. Preferred heterocyclic rings are saturated. Heterocyclic rings may be substituted or unsubstituted, preferably unsubstituted. Preferred heterocyclic rings are saturated analogs of the above-specified heteroaryl rings, especially tetrahydrofuryl.

As used herein, "substituted", in reference to alkyl, aryl, heteroaryl or heterocyclic groups, means such groups that can be mono- or polysubstituted. Preferred is mono-, di- or trisubstituted; more preferred is monosubstituted. Preferred substituents are selected from the group consisting of halogen, hydroxy, amino, nitro, thiol, aryl, alkyl and —OR wherein —R is aryl or alkyl.

As used herein, "biochemical damage" means damage (resulting in a possible impact on such cell activities as membrane function, metabolism, and gene expression) to compounds of any biochemical class, including, but not limited to, nucleic acids, proteins and free amino acids, lipids and lipoproteins, carbohydrates, and connective tissue macromolecules.

As used herein, "cellular damage" means damage to cell activities including, but not limited to, membrane function, metabolism, and gene expression.

As used herein, "chelation" means the removal of a metal ion from a system by forming a complex so that the metal ion cannot readily participate in or catalyze chemical reactions.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

As used herein when referring to composition ingredients, "compatible" means that the particular ingredient in question is capable of being commingled with the chelating agent and other ingredients in a manner such that there is no interaction which would substantially reduce the efficacy of the composition of the present invention.

As used herein, "free radical" means an atom or group of atoms with an unpaired electron.

As used herein, "free radical reaction" means the reaction of a free radical with another substance.

As used herein, "parenteral administration" means introduction of a composition by injection, such as intraperitoneal, intravenous, subcutaneous, intramuscular, or intramedullary.

As used herein, "regulating" means preventing, retarding, or arresting.

As used herein, "safe and photoprotectively effective amount" means an amount of agent or composition sufficient to substantially reduce the deleterious effects of UV-radiation to skin but not so much as to cause serious side effects or adverse skin reactions.

As used herein, all percentages are by weight unless otherwise specified.

Although the present invention is not limited to any particular mechanism, it is believed that the present invention works wholly or partly by operation of the following mechanism. Certain metal chelators are able to "tie-up" free iron or facilitate its removal from a target tissue, thus impairing its catalytic activity, thus protecting the skin from aging effects caused by UV exposure. By "tying up" free iron, the solubility of the iron is changed and therefore may be removed from that tissue and subsequently excreted or removed to a tissue where damage is less likely. In addition, by impairing the catalytic activity of metal ions in the human body, the compositions of the present invention prevent, arrest, or retard diseases and disorders in living beings in which free radicals, particularly oxygen radicals, have been implicated as a pathogen. For example, various insults to a person's body (e.g., injury, disease, or U.V. irradiation) lead to small amounts of free radical formation. These small amounts of free radicals may be amplified catalytically by transition metals in the body, such as iron. The resulting free radicals may be more reactive, toxic and deleterious to biological tissue. In addition, the increased concentration of free radicals may also result in more deleterious effects to biological tissue. For further examples of free radical reactions, see Cross, C. E., G. Halliwell, E. T. Borish, W. A. Pryor, B. N. Ames, R. L. Saul, J. M. McCord, and D. Harmon, "Oxygen Radicals and Human Disease", 107 *Annals of Internal Medicine* 526 (1987).

Chelating agents useful in compositions and methods of the present invention have the following structural formula:

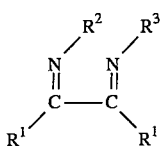 (I)

wherein each —$R^1$ is independently selected from the group consisting of alkyl, aryl, heteroaryl and heterocyclic, or the —$R^1$'s are covalently bonded together to form a cyclic alkyl or heterocyclic ring; —$R^2$ and —$R^3$ are —$OR^4$, in which case there is no bond or a polar bond between —$R^2$ and the nitrogen covalently bonded to —$R^3$, each —$R^4$ being independently selected from the group consisting of hydrogen, alkyl and aryl except that both —$R^4$'s are not methyl when both —$R^1$'s are furyl; or —$R^2$ is —O— and is covalently bonded to the nitrogen which is covalently bonded to —$R^3$, and —$R^3$ is —O— (there being a + charge on the nitrogen to which it is bonded) or nil; wherein the compounds consist essentially of compound wherein =$NR^2$ and =$NR^3$ are in amphi configuration when both —$R^2$ and —$R^3$ are —OH, and when both —$R^1$'s are furyl or the —$R^1$'s are covalently bonded together to form a cyclohexanedione structure.

Preferably both —$R^1$'s are the same moiety. Preferably both —$R^4$'s are the same moiety.

When —$R^1$ is aryl, —$R^1$ is preferably selected from substituted and unsubstituted, preferably unsubstituted, 2-hydroxyphenyl and phenyl.

When —$R^1$ is heteroaryl, —$R^1$ is preferably selected from substituted and unsubstituted, preferably unsubstituted, 2-furyl, 3-furyl, 2-thienyl, 3-thienyl, 2-pyrrolyl, 2-imadazolyl, 1-pyrazolyl, 2-pyrazinyl, 2-pyrimidinyl, 3-pyridazinyl, 3-isoquinolyl, 8-purinyl, 1-phthalazinyl, 2-quinoxalinyl, 3-furazanyl, 3-isoxazolyl, 2-tetrazolyl and 5-tetrazolyl; more preferably from 2-furyl, 3-furyl, 2-thienyl, 3-thienyl and 2-pyrrolyl; more preferably still from 2-furyl and 3-furyl. Most preferably —$R^1$ is 2-furyl.

When —$R^1$ is heterocyclic, —$R^1$ is preferably the saturated analog of the preferred heteroaryls specified in the previous paragraph; most preferred is 2-tetrahydrofuryl.

When —$R^1$ is alkyl, —$R^1$ is preferably selected from substituted and unsubstituted, preferably unsubstituted, $C_1$–$C_{20}$ alkyl, more preferably $C_1$–$C_{18}$, more preferably $C_1$–$C_{12}$, more preferably still $C_1$–$C_6$, more preferably $C_1$–$C_2$, most preferably $C_1$. Preferred alkyl —$R^1$'s are alkanyls. Preferred alkanyls are straight chain.

When —$R^1$ is substituted, each substituent is preferably selected from alkyl and aryl. When the substituent is an alkyl, it is preferably selected from $C_1$–$C_{20}$ alkyl, more preferably $C_1$–$C_{18}$, more preferably $C_1$–$C_{12}$, more preferably still $C_1$–$C_6$, more preferably $C_1$–$C_2$, most preferably $C_1$. When the substituent is an aryl, it is preferably phenyl.

Preferred chelating agents useful in the present invention include those having the following structural formula:

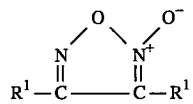

wherein —$R^1$ is as defined hereinabove.

Preferred chelating agents useful in the present invention include those having the following structural formula:

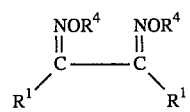

wherein —$R^1$ and —$R^4$ are as defined hereinabove. Preferably such compounds are in the amphi configuration.

Most preferably —$R^4$ is hydrogen.

When —$R^4$ is aryl, it is unsubstituted or substituted, preferably unsubstituted; preferably —$R^4$ is phenyl. When —$R^4$ is a substituted aryl, the substituent is preferably —OH.

When —$R^4$ is alkyl, it is unsubstituted or substituted, preferably unsubstituted, preferably selected from $C_1$–$C_{20}$, more preferably $C_2$–$C_{18}$, more preferably $C_2$–$C_{12}$, more preferably $C_2$–$C_6$, more preferably still $C_2$–$C_4$, most preferably $C_2$. When —$R^4$ is a substituted alkyl, preferred substituents are selected from —OH, =O, carboxy, —$NH_2$, —$NHR^7$ and —$NR^7_2$, wherein —$R^7$ is alkyl or aryl.

Preferred compounds for use in the present invention include di-(2-furyl) ethanedione amphi-dioxime, di-(5-methyl-2-furyl) ethanedione amphi-dioxime, di-(4-methyl-2-furyl) ethanedione amphi-dioxime, di-(5-ethyl-2-furyl) ethanedione amphi-dioxime, di-(4-ethyl-2-furyl) ethanedione amphi-dioxime, di-(5-propyl-2-furyl) ethanedione amphi-dioxime, and di-(4-propyl-2-furyl) ethanedione amphi-dioxime; more preferred are di-(2-furyl) ethane-dione amphi-dioxime, di-(5-methyl-2-furyl) ethanedione amphidioxime, di-(4-methyl-2-furyl) ethanedione amphi-dioxime, di-(5-ethyl-2-furyl) ethanedione amphi-dioxime, and di-(4-ethyl-2-furyl) ethanedione amphi-dioxime; still more preferred is di-(2-furyl) ethanedione amphi-dioxime. Representative structures include

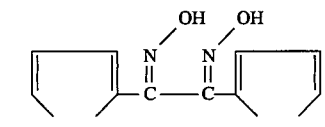
di-(2-furyl) ethanedione amphi-dioxime,

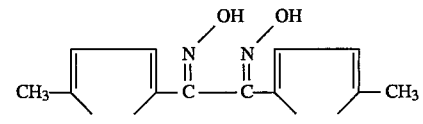
di-(5-methyl-2-furyl) ethanedione amphi-dioxime, and

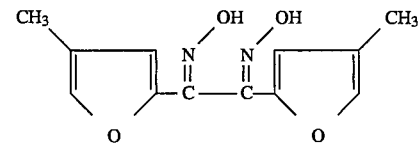
di-(4-methyl-2-furyl) ethanedione amphi-dioxime.

Compounds also preferred for use in the present invention include di-(2-thienyl) ethanedione amphi-dioxime, di-(5-methyl-2-thienyl) ethanedione amphi-dioxime, di-(4-methyl-2-thienyl) ethanedione amphi-dioxime, di-(5-ethyl-2-thienyl) ethanedione amphi-dioxime, and di-(5-propyl-2-thienyl) ethanedione amphidtoxime; more preferred are di-(2-thienyl) ethanedione amphi-dioxime, di-(5-methyl-2-thienyl) ethanedione amphi-dioxime, and di-(4-methyl-2-thienyl) ethanedione amphi-dioxime; still more preferred is di-(2-thienyl) ethanedione amphi-dioxime. Representative structures include:

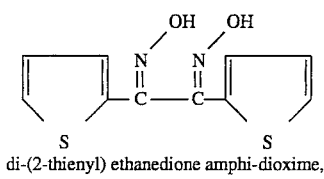
di-(2-thienyl) ethanedione amphi-dioxime,

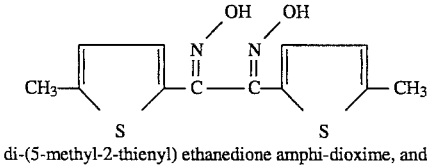
di-(5-methyl-2-thienyl) ethanedione amphi-dioxime, and

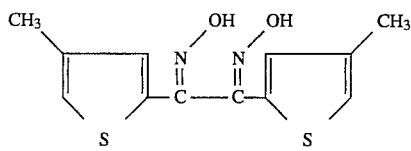
di-(4-methyl-2-thienyl) ethanedione amphi-dioxime.

Compounds also preferred for use in the present invention include di-(2-pyrrolyl) ethanedione amphi-dioxime, di-(5-methyl-2-pyrrolyl) ethanedione amphi-dioxime, di-(4-methyl-2-pyrrolyl) ethanedione amphi-dioxime, di-(5-ethyl-2-pyrrolyl) ethanedione amphi-dioxime, di-(4-ethyl-2-pyrrolyl) ethanedione amphi-dioxime, di-(5-propyl-2-pyrrolyl) ethanedione amphi-dioxime, and di-(5-propyl-2-pyrrolyl) ethanedione amphi-dioxime; more preferred are di-(2-pyrrolyl) ethanedione amphi-dioxime, di-(5-methyl-2-pyrrolyl) ethanedione amphi-dioxime, di-(4-methyl-2-pyrrolyl) ethanedione amphi-dioxime, di-(5-ethyl-2-pyrrolyl) ethanedione amphi-dioxime, and di-(4-ethyl-2-pyrrolyl) ethanedione amphidioxime; still more preferred are di-(2-pyrrolyl) ethanedione amphi-dioxime, di-(5-methyl-2-pyrrolyl) ethanedione amphi-dioxime, and di-(4-methyl-2-pyrrolyl) ethanedione amphi-dioxime; more preferred still is di-(2-pyrrolyl) ethanedione amphi-dioxime. Representative structures include

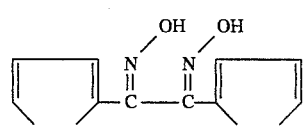
di-(2-pyrrolyl) ethanedione amphi-dioxime,

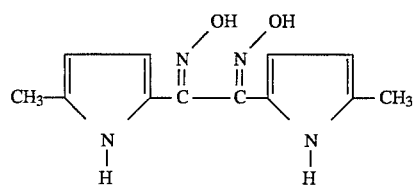
di-(5-methyl-2-pyrrolyl) ethanedione amphi-dioxime, and

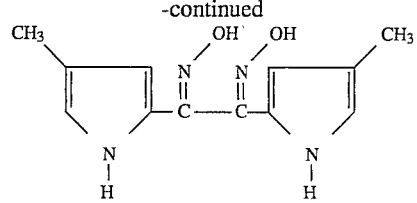
di-(4-methyl-2-pyrrolyl) ethanedione amphi-dioxime.

Compounds also preferred for use in the present invention include di-(1-methyl-2-pyrrolyl) ethanedione amphi-dioxime, di-(1,5-dimethyl-2-pyrrolyl) ethanedione amphi-dioxime, di-(1-methyl-5-ethyl-2-pyrrolyl) ethanedione amphi-dioxime, di-(1-methyl-5-propyl-2-pyrrolyl) ethanedione amphi-dioxime, and di(1-methyl-2-pyrrolyl) ethanedione amphi-dioxime; more preferred are di-(1-methyl-2-pyrrolyl) ethanedione amphi-dioxime, di-(1,5-dimethyl-2-pyrrolyl) ethanedione amphi-dioxime, di-(1-methyl-dimethyl-2-pyrrolyl) ethanedione amphi-dioxime, di-(1-methyl-5-propyl-2-pyrrolyl) ethanedione amphi-dioxime; still more preferred is di-(1-methyl-2-pyrrolyl) ethanedione amphi-dioxime. Representative structures include:

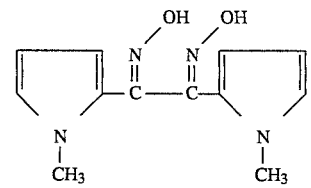
di-(1-methyl-2-pyrrolyl) ethanedione amphi-dioxime,

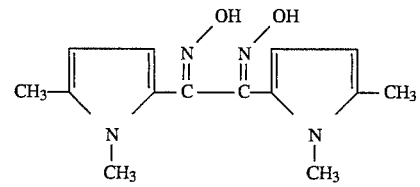
di-(1,5-dimethyl-2-pyrrolyl) ethanedione amphi-dioxime, and

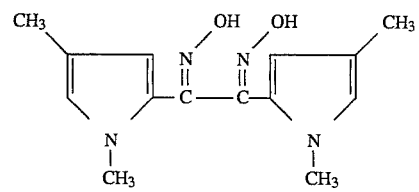
di-(1,4-methyl-2-pyrrolyl) ethanedione amphi-dioxime.

Compounds also preferred for use in the present invention include:

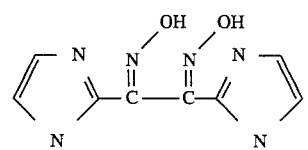
di-(2-imadazolyl) ethanedione amphi-dioxime,

-continued

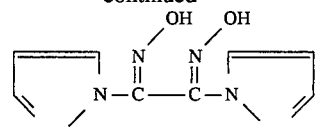
di-(1-pyrazolyl) ethanedione amphi-dioxime,

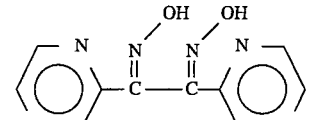
di-(2-pyrazinyl) ethanedione amphi-dioxime,

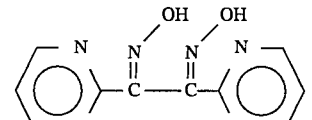
di-(2-pyrimidinyl) ethanedione amphi-dioxime.

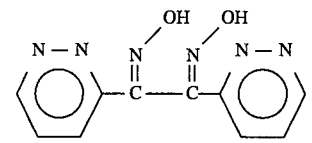
di-(3-pyridazinyl) ethanedione amphi-dioxime,

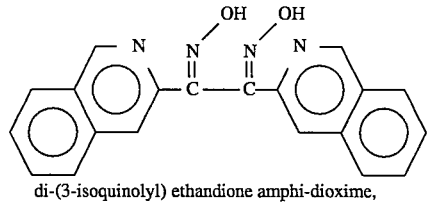
di-(3-isoquinolyl) ethandione amphi-dioxime,

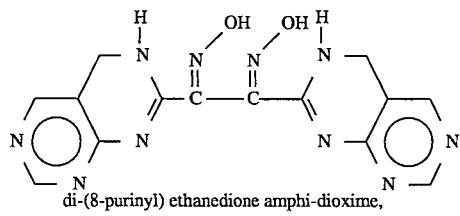
di-(8-purinyl) ethanedione amphi-dioxime,

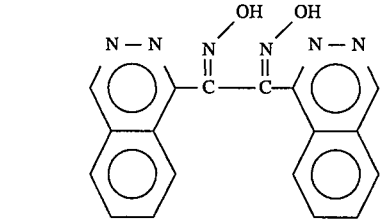
di-(1-phthalazinyl)ethanedione amphi-dioxime,

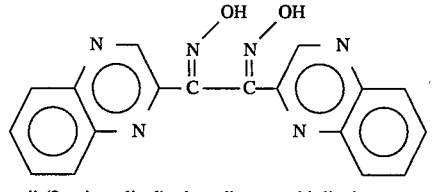
di-(2-quinoxalinyl) ethanedione amphi-dioxime,

-continued

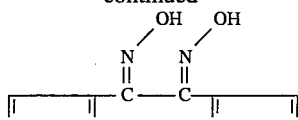
di-(3-furazanyl) ethanedione amphi-dioxime,

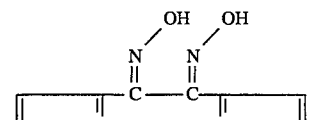
di-(3-isoxazolyl) ethanedione amphi-dioxime,

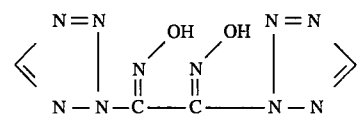
di-(2-tetrazolyl) ethanedione amphi-dioxime,

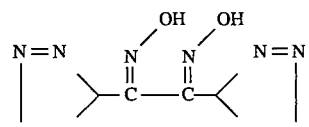
di-(5-tetrazolyl) ethanedione amphi-dioxime.

Compounds also preferred for use in the present invention include di-(4-ethylphenyl) ethanedione amphi-dioxime, di-(3-ethylphenyl) ethanedione amphi-dioxime, di-(4-propylphenyl) ethanedione amphi-dioxime, di-(2-hydroxy) ethanedione amphi-dioxime, and di-(2-hydroxy-4-ethylphenyl) ethanedione amphi-dioxime; more preferred are di-(4-ethylphenyl) ethanedione amphi-dioxime, di-(3-ethylphenyl) ethanedione amphi-dioxime, di-(4-propylphenyl) ethanedione amphi-dioxime; still more preferred is di-(4-ethylphenyl) ethanedione amphi-dioxime. Representative structures include:

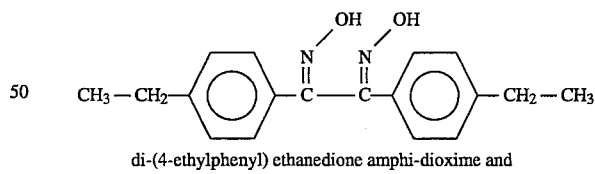
di-(4-ethylphenyl) ethanedione amphi-dioxime and

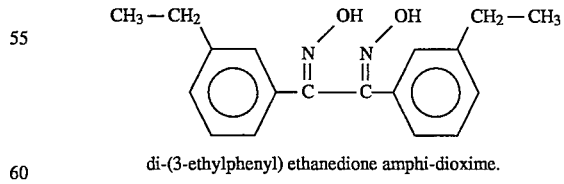
di-(3-ethylphenyl) ethanedione amphi-dioxime.

Compounds also preferred for use in the present invention include 4,5-di-(2-furyl) furoxan and 4,5-di-(2-thienyl) furoxan; preferably 4,5-di-(2-furyl) furoxan, a representative structure of which is as follows:

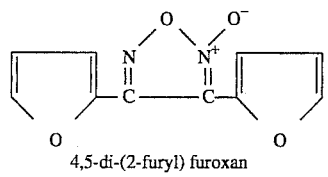

4,5-di-(2-furyl) furoxan

Also preferred for incorporation in the compositions of the present invention are mixtures of any of the above compounds.

A compound also preferred for use in the present invention is amphi-1,2-cyclohexanedione, which is represented by the following structure

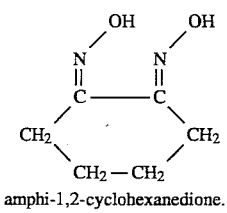

amphi-1,2-cyclohexanedione.

Also preferred for incorporation in the compositions of the present invention are mixtures of the above amphi-form compounds, except for di-(2-furyl) ethanedione amphi-dioxime and amphi-1,2-cyclohexanedione, with their corresponding anti- and syn-forms. Typically such mixtures are about half amphi-form and about half anti-form with very little (less than about 2%) syn-form. For compounds named herein, lack of designation of a particular form is non-specific and denotes either the amphi-form alone or a mixture of it with the other forms; any such mixture is preferably at least 40% amphi-form, more preferably at least 60% amphi-form, more preferably still at least 80% amphi-form.

Another aspect of the present invention relates to novel compounds having the structural formula

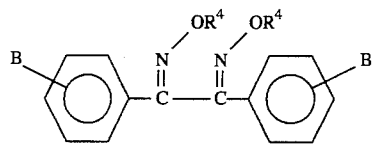

wherein —$R^4$ is as defined as hereinbefore; —B is independently selected from the group consisting of alkyl, aryl, or heteroaryl; preferably alkyl; more preferably $C_2$–$C_{20}$ alkyl; more preferably a $C_2$–$C_6$ alkyl; more preferably ethyl. —B is preferably bonded to the 4-position.

Another aspect of the present invention relates to novel compounds having the structural formula

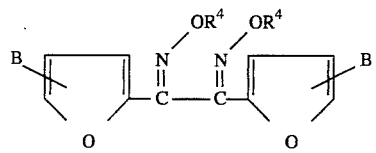

wherein —$R^4$ and —B are as defined hereinbefore; —B is preferably bonded to the 5-position, Another aspect of the present invention relates to novel compounds having the structural formula:

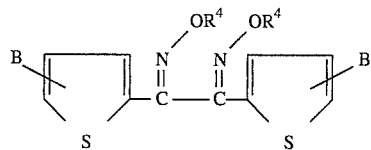

wherein —$R^4$ and —B are as defined hereinbefore; —B is preferably bonded to the 5-position.

Test Method I

Standard Method for Assay of Ornithine Decarboxylase

Scope: This method describes an assay procedure for the determination of the enzyme ornithine decarboxylase (ODC) in mouse skin epidermis. The assay is linear up to at least 40 minutes of incubation of enzyme with substrate, with a deviation between replicates of less than 10%. The method is based on published procedures for determination of mouse epidermal ODC. (See Lowe, N., A. K. Verma, and R. K. Boutwell, *Journal of Investigational Dermatology*, Vol. 71 (1978), pp. 417–418; Verma, A. K., N. J. Lowe & R. K. Boutwell, *Cancer Research*, Vol. 39 (1979), pp. 1035–1040; Binder, R. L., N. E. Volpenheim & A. A. Motz, *Carcinogenesis*, Vol. 10 (1989), pp. 2351–2357; and Hillebrand, G. G., N. S. Winslow, M. J. Benzinger, D. A. Heitmeyer & D. L. Bissett, "Acute and Chronic Ultraviolet Radiation Induction of Epidermal Ornithine Decarboxylase Activity in Hairless Mice", *Cancer Research*, Vol. 50 (1990) pp. 1580–1584.

Principle: A homogenate of mouse epidermal tissue is incubated with carbon 14-labeled L-ornithine, the substrate for the enzyme. The enzyme catalyzes the release from ornithine of $^{14}CO_2$, which is trapped with benzethonium hydroxide. The $^{14}C$ is then counted versus substrate to determine amount of liberated $CO_2$. The amount of liberated $CO_2$ is used to determine the level of enzyme present in the tissue. There are no available standards for this mouse skin enzyme. Previous work (see Hillebrand) has indicated the conditions under which this assay can be done to obtain a linear correspondence between time of enzyme-substrate incubation and release of $^{14}CO_2$.

Chemicals:
1. $NaH_2PO_4 \cdot H_2O$
2. $Na_2HPO_4 \cdot 7H_2O$
3. EDTA (ethylene diamine tetracetic acid), disodium, dihydrate
4. PLP (pyridoxal phosphate)
5. DTT (dithiothreitol)
6. L-ornithine.HCl
7. L-[1-$^{14}C$]-ornithine.HCl (52 mCi/mmole; Dupont NEN Products, Boston, Mass.)
8. Anhydrous citric acid
9. Methylbenzethonium hydroxide (1M solution in methanol; Sigma Chemical Co., St. Louis, Mo.)
10. Bio-Rad Protein Assay Kit—based on Bradford protein assay (See Randford, M., *Anal. Biochemistry*, Vol. 72 (1976), p. 248.)

See note at end of method.

Equipment:
1. Clear polystyrene tubes (12×75 mm, #14-956-3D,

Fisher Scientific, Pittsburgh, Pa.)
2. Tissue homogenizer - Tissuemizer (type SDT-1810, Tekmar, Co., Cincinnati, Ohio)
3. 1.5 ml polypropylene micro test tubes (#223-9500, Bio-Rad Laboratories, Richmond, Calif.)
4. Eppendorf centrifuge (model 5415; Brinkman Instruments Inc., Westbury, N.Y.)
5. Pasteur pipettes.
6. Cryogenic vials (#07753-0308), Vangard Cryos, Vangard International Inc., Neptune, N.J.)
7. 15×85 mm and 16×150 mm glass test tubes
8. 37° C. shaking water (Aquatherm water bath shaker model R-86, New Brunswick Scientific Co., New Brunswick, N.J.)
9. Kontes Scientific (Vineland, N.J.) rubber stoppers (#882310-0000) and center well assemblies (#882320-0000)
10. Magnetic stirrer and Teflon-coated magnetic stir bars
11. Glass beakers (100, 250 and 500 ml sizes, and 1 and 2 liter sizes)
12. 50 ml polypropylene centrifuge tubes (#25331, Corning Glass Works, Corning, N.Y.)
13. Vortex mixer
14. Spectrophotometer (model 260, Gilford Instrument Laboratories, Inc., Oberlin, Ohio)
15. Whatman No. 1 filter paper
16. Polypropylene funnel See note at end of method.

Preparation of Special Reagents:
1. Homogenization buffer: Homogenization buffer=50 mM sodium phosphate, 1.25 mM EDTA, 2.5 mM DTT and 0.1 mM PLP [pH 7.1].
    (a) Dissolve 3.45 g of $NaH_2PO_4.7H_2O$ and 0.23 g EDTA in 400 ml of distilled-deionized water; bring volume to 500 ml:
        50 mM monobasic sodium phosphate+1.25 mM EDTA.
    (b) Dissolve 6.7 g of $Na_2HPO_4.H_2O$ and 0.23 g of EDTA in 400 ml of distilled-deionized water; bring volume to 500 ml:
        50 mM dibasic sodium phosphate+1.25 mM EDTA.
Combine 250 ml of (a) with 500 ml of (b) to yield 750 ml of pH 7.1 phosphate-EDTA buffer. Add 0.289 g of DTT to 750 ml of phosphate-EDTA buffer and then 0.0185 g of PLP to 750 ml of phosphate-EDTA-DTT buffer to prepare final homogenization buffer. This is prepared in advance and kept frozen at −20° C. in 50-ml aliquats in 50 ml polypropylene centrifuge tubes until needed. Then it is thawed, and kept on ice.
2. Substrate solution: Substrate solution=1.6 mM L-ornithine, 0.65 mM PLP, 20 micro Ci/ml L-[$^{14}$C]-ornithine.
Dissolve 34 mg of L-ornithine in 100 ml of water. To this is added 20 mg of PLP. This is frozen in 1-ml aliquats until used. Mix 1 ml of the ornithine-PLP mixture with 0.25 ml (25 micro Ci) of L-[1-$^{14}$C]-ornithine hydrochloride (52 mCi/mmole; Dupont NEN Products, Boston, Mass.). This substrate solution is de-gassed (to remove any $^{14}CO_2$) by pulling a partial vacuum (aspirator) on the solution three times, each of 30 seconds duration. This solution is then kept at room temperature until used.
3. Citric acid solution: Dissolve 384 g of citric acid in 600 ml of water; bring the volume up to 1000 ml: 2M citric acid (pH 1.5). This is prepared in advance and kept frozen at −20° C. in 50-ml aliquats in 50 ml polypropylene centrifuge tubes until needed. Then it is thawed, and kept at room temperature.
4. Dye Reagent: Dilute 1 volume of Dye Reagent Concentrate with 4 volumes of distilled-deionized water. Filter through Whatman No. 1 filter paper and store dilute reagent in a glass container at room temperature. Prepare just before use.
5. Protein standard: The Bio-Rad Protein Standard supplied in the kit is lyophilized bovine protein sealed under nitrogen. To reconstitute, add 20 ml of distilled-deionized water which will yield a protein concentration of 1.4 mg/ml. This protein solution is stored at −20° C. until needed. Then it is thawed, and kept at room temperature.

Mouse Treatment and Irradiation. A chelator to be screened is dissolved in a liquid vehicle; preferred vehicles are ethanol, isopropanol, water, propylene glycol, or mixtures thereof. The test material solution is 5% (w/v) chelator (or saturated with chelator if the chelator is not soluble at 5% in any reasonable vehicle).

Test material solutions are applied topically to the dorsal skin of the mouse. A control group of mice receives topical application of the same vehicle as is in the test material solution (without the chelating agent). Test material solution or control vehicle is applied to the skin of each mouse at an application rate of approximately 2 $\mu l/cm^2$. Topical treatments are done three times: AM and PM of Day 1 and AM of Day 2.

Two hours after the third treatment, the dorsal skin of the mice is exposed to 2X MED (minimum erythemal dose) with a 1000-watt Xenon arc solar simulator. The total UV dose is approximately 1.6 $J/cm^2$. Twenty-four hours after irradiation, mice are sacrificed by cervical dislocation, and the dorsal skin is removed.

Procedure:
1. Whole dorsal skin from a mouse is placed dermis side down on an ice cold glass plate. The epidermal side of the skin is scraped with a razor blade 20 times to remove the epidermis, which adheres to the razor blade.
2. Epidermal shave scrapings are transferred to individual 12× 75 mm clear polystyrene tubes containing 0.6 ml of ice cold homogenization buffer.
3. Using a Tissuemizer homogenizer, the tissue is homogenized on ice for 20 seconds at a homogenizer power control setting of 80 (0–100 scale).
4. The homogenate is transferred to a 1.5 ml polypropylene micro test tube and centrifuged at 16,000×g for 10 minutes at 4° C. in an Eppendorf centrifuge.
5. The clear supernatant solution is transferred with a Pasteur pipette to a 1.2 cc cryogenic vial.
6. Add 0.1 ml of supernatant solution to a 15×85 mm glass test tube and place in a 37° C. shaking water bath for 5 minutes. Duplicate assays are run for each sample. Six blank assays containing 0.1 ml of homogenization buffer are also run.
7. The assay is started by addition of 0.025 ml of de-gassed substrate solution. This gives a final concentration of assay components of 40 mM sodium phosphate, 1 mM EDTA, 2 mM DTT, 0.2 mM PLP, 0.4 mM ornithine, and 0.5 micro Ci of $^{14}$C-ornithine. The assay tube is immediately sealed with a rubber stopper and center well assembly, the center well containing 0.1 ml of methylbenzethonium hydroxide. The reaction is run at 37° C. in a shaker water bath at 50 rpm for 30 minutes.

8. Using a disposable 1 ml plastic syringe fitted with a 22 gauge 1.5-inch needle, the assay is stopped by piercing the rubber stopper and injecting 0.25 ml of 2M citric acid solution into the assay solution. Particular care is taken not to inject citric acid into the center well assembly.

9. The assay mixture is kept at room temperature for 30 minutes after citric acid injection to ensure complete absorption of $^{14}CO_2$ by methylbenzethonium hydroxide contained in the center well.

10. The center well bucket is transferred, by cutting with scissors the center well stem, to scintillation vials containing 10 ml of scintillation fluid and shaken thoroughly. Standards are prepared by adding 0.025 ml of substrate solution to 10 ml of scintillation fluid; this amount of $^{14}C$ represents total conversion of substrate to $CO_2$ in the assay.

11. Content of $^{14}C$ is determined with a scintillation counter.

12. Determine protein content of homogenate by the Bio-Rad Protein Assay. Place 0.02 ml of homogenate and 0.08 ml of water in a test tube (16×150 mm). As blanks, 0.02 ml of homogenization buffer is used. All assays are done in duplicate. Add 5 ml of diluted dye reagent. Mix on a vortex mixer. After 5 minutes to 1 hour, measure $OD_{595}$ versus blanks. Protein content of samples is read from a plot of $OD_{595}$ versus concentration of protein standards (20–140 microgram).

Calculations: Based on the total dpm in the L-[$^{14}C$]-ornithine standard, the dpm per pmole of $^{14}C$ can be derived. The following equations are then used to calculate ODC activity on the basis of protein:

$$\frac{\text{dpm sample} - \text{dpm blank}}{\text{dpm/pmole } ^{14}C \times 0.1 \text{ ml} \times 0.5 \text{ hour} \times \text{mg protein/ml}} = \frac{\text{pmole}}{\text{hr mg}}$$

The Ornithine Decarboxylase (ODC) value (pmole/hr mg) for the chelator being screened is compared to the ODC value (pmole/hr mg) for the control to give a percent difference between the two values. Preferred compounds useful in the present invention demonstrate at least a 20% decrease in the ODC value as compared to the ODC value of the control.

NOTE: The chemicals and equipment specified in these sections are described in detail as to properties, dimensions, and suggested suppliers for the convenience of those doing the assay. Unless otherwise indicated, alternate sources of equivalent chemicals and equipment may be used, providing that they meet the requirements necessary to preserve the accuracy and precision of the assay method.

Test Method II

In Vivo Mouse Skin Wrinkling Test

A second test useful for screening chelators for photoprotective capability is the in vivo mouse skin wrinkling test which measures premature wrinkling inhibition, described in D. L. Bissett, D. P. Hannon & T. V. Orr, "An Animal Model of Solar-Aged Skin: Histological, Physical, and Visible Changes in UV-Irradiated Hairless Mouse Skin", *Photochem. Photobiol.*, Vol. 46 (1987), pp. 367–378; and D. L. Bissett, G. G. Hillebrand and D. P. Hannon, "The Hairless Mouse as a Model of Skin Photoaging: Its Use to Evaluate Photoprotective Materials", *Photodermatology*, Vol. 6 (1989), pp. 228–233.

The test is used to determine the photoprotective efficacy of topically applied materials against UVB-induced photoaging. The work is done with Skh:HR-1 hairless mice.

A chelator to be screened is dissolved in a liquid vehicle; preferred vehicles are ethanol, isopropanol, water, propylene glycol, or mixtures thereof. The test material solution is 5% (w/v) chelator (or saturated with chelator if the chelator is not soluble at 5% in any reasonable vehicle).

Test material solutions are applied topically to the dorsal skin of the mouse. A control group of mice receives topical application of the same vehicle as is in the test material solution (without the chelating agent). Test material solution or control vehicle is applied to the skin of each mouse at an application rate of approximately $2/\mu l/cm^2$. Topical treatments are done three times each week.

A bank of four 4-foot fluorescent UVB lamps (Westinghouse FS-40 sunlamps) is used. The energy output of the lamps is measured with an International Light (Newburyport, Mass.) model 700 A research radiometer. Mice are irradiated with 30 mJ/cm$^2$ of UVB per exposure. Irradiations are done two hours after each topical application of the test material solution or vehicle.

Once each week, mice are observed for skin wrinkling and tumor formation (see Bissett, et al., *Photochem. Photobiol.*, Vol. 46 (1987), pp. 367–378 and Bissett, et al., *Photodermatology, Vol.* 6 (1989), pp. 228–233. Wrinkles are graded on a 0–3 scale, and tumors are counted as described in these references. The test is continued until the skin wrinkle grade of the control group is at least about 2.0 and the tumors are recounted at this point; generally the test requires about 20 weeks to complete.

Chelating agents which exhibit at least about a 20% reduction in skin wrinkle grade in Test Method II are useful in the present invention. Preferred chelating agents exhibit at least about a 30% reduction in skin wrinkle grade; more preferred chelating agents exhibit at least about a 60% reduction in skin wrinkle grade; most preferred chelating agents exhibit at least about a 90% reduction in skin wrinkle grade.

A composition of the present invention may be tested using Test Method II to determine its effective dosage levels and appropriate formulations and methods of application. For example, if a chelator shown to be effective using Test Method I is shown in Test Method II to be a relatively ineffective photoprotective agent due to its inability to penetrate the skin, it may be formulated with a skin penetration enhancer to enhance its efficacy.

A safe and effective amount of a chelating agent is used in the compositions of the present invention. Typically, this is from about 0.1% to about 10%, preferably from about 0.5% to about 5% of the composition.

It is important to note that, when used for purposes of photoprotection, the chelating agent is predominantly a non-sunscreen photoprotecting agent. A sunscreen works on the surface of the skin to absorb UV radiation so that the harmful rays never enter the skin. The chelating agent works in the skin to prevent damaging reactions in the skin. Because the chelating agent penetrates the skin to work, rub-off, wear-off or wash-off of the active, which lessen efficacy for sunscreens considerably, are essentially irrelevant with the present invention. Furthermore, though critical with a sunscreen, it is not necessary to keep an even coating of the active of the present invention on the skin for the entire exposure period. The chelating agent can be applied to the skin up to four hours or longer prior to UV exposure. The chelating agent protects against both acute effects of UV exposure, e.g., sunburn, and chronic effects of UV exposure, e.g., premature aging of the skin.

Carriers

In addition to the chelating agent as described hereinbefore, the pharmaceutical compositions of the present invention essentially comprise a pharmaceutically-acceptable carrier. The term "pharmaceutically-acceptable carrier", as used herein, means one or more compatible solid or liquid filler diluents or encapsulating substances which are suitable for administration to a human or lower animal. Pharmaceutically-acceptable carriers must, of course, be of sufficiently high purity and sufficiently low toxicity to render them suitable for administration to the human or lower animal being treated. A safe and effective amount of carrier is from about 80% to about 99%, preferably from about 90% to about 98%, of the composition.

Variations in formulation of these carriers will result in a wide variety of products which fall within the scope of the present invention.

A. Topical Carriers

The topical pharmaceutical/cosmetic compositions of the present invention may be made into a wide variety of product types. These include, for example, lotions, creams, beach oils, gels, sticks, sprays, ointments, pastes, mousses and cosmetics. These product types may comprise either of two basic types of carrier systems, solutions and emulsions.

The topical pharmaceutical/cosmetic compositions of the present invention formulated as solutions typically include a pharmaceutically- or cosmetically-acceptable aqueous or organic solvent. The terms "pharmaceutically-acceptable aqueous solvent", "cosmetically-acceptable aqueous solvent", "pharmaceutically-acceptable organic solvent" and "cosmetically-acceptable organic solvent" refer to a solvent which, in addition to being capable of having dispersed or dissolved therein the chelating agent, also possesses acceptable safety (e.g., irritation and sensitization characteristics), as well as good aesthetic properties (e.g., does not feel greasy or tacky). Water is a typical aqueous solvent. Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, butanediol, and mixtures thereof. These solutions contain from about 0.01% to about 20%, more preferably from about 0.5% to about 10%, more preferably from about 1% to about 5% of the chelating agent, and from about 80% to about 99.99%, more preferably from about 90% to about 99.5%, more preferably from about 95% to about 99% of an acceptable organic solvent.

If the topical pharmaceutical/cosmetic compositions of the present invention are formulated as an aerosol and applied to the skin as a spray-on, a propellant is added to a solution composition. Examples of propellants useful herein include, but are not limited to, the chlorinated, fluorinated and chloro-fluorinated lower molecular weight hydrocarbons. A more complete disclosure of propellants useful herein can be found in Sagaran, *Cosmetics Science and Technology*, 2nd Edition, Vol. 2, pp. 443–465 (1972).

Topical pharmaceutical/cosmetic compositions of the present invention may be formulated as a solution comprising an emollient. An example of a composition formulated in this way would be a beach oil product. Such compositions contain from about 0.1% to about 20% of the chelating agent and from about 1% to about 50% of a topical pharmaceutically/cosmetically-acceptable emollient.

As used herein, "emollients" refer to materials used for the prevention or relief of dryness, as well as for the protection of the skin. A wide variety of suitable emollients are known and may be used herein. Sagaran, *Cosmetics, Science and Technology*, 2nd Edition, Vol. 1, pp. 32–43 (1972), incorporated herein by reference, contains numerous examples of suitable materials.

A lotion can be made from a solution carrier system. Lotions typically comprise from about 0.1% to about 20%, preferably from about 0.5% to about 10%, of the chelating agent; from about 1% to about 20%, preferably from about 5% to about 10%, of an emollient; and from about 50% to about 90%, preferably from about 60% to about 80%, water. Another type of product that may be formulated from a solution carrier system is a cream. A cream of the present invention would comprise from about 0.1% to about 20%, preferably from about 0.5% to about 10%, of the chelating agent; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Segarin, *Cosmetics, Science and Technology*, 2nd Edition, Vol. 1, pp. 72–73 (1972).

If the carrier is formulated as an emulsion, from about 1% to about 10%, preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's *Detergents and Emulsifiers*, North American Edition, pages 317–324 (1986); the disclosures of which are incorporated herein by reference. Preferred emulsifiers are anionic or nonionic, although the other types may also be used.

Single emulsion skin care preparations, such as lotions and creams, of the oil-in-water type and water-in-oil type are well-known in the cosmetic art and are useful in the present invention. Multiphase emulsion compositions, such as the water-in-oil-in-water type, as disclosed in U.S. Pat. No. 4,254,105, Fakuda et al., issued Mar. 3, 1981, herein incorporated by reference, are also useful in the present invention. In general, such single or multiphase emulsions contain water, emollients and emulsifiers as essential ingredients.

Triple emulsion carrier systems comprising an oil-in-water-in-silicone fluid emulsion composition as disclosed in U.S. Pat. No. 4,960,764, herein incorporated by reference, are also useful in the present invention. This triple emulsion carrier system can be combined with from about 0.1% to about 20%, preferably from about 0.5% to about 10%, of the chelating agent to yield the topical pharmaceutical/cosmetic composition of the present invention.

Another emulsion carrier system useful in the topical pharmaceutical/cosmetic compositions of the present invention is a micro-emulsion carrier system. Such a system comprises from about 9% to about 15% squalane; from about 25% to about 40% silicone oil; from about 8%, to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with from about 0.5% to about 10% of the chelating agent.

Lotions and creams can be formulated as emulsions as well as solutions. Typically such lotions comprise from about 0.1% to about 20%, preferably from about 0.5% to about 10%, of the chelating agent; from about 1% to about 20%, preferably from about 5% to about 10%, of an emollient; from about 25% to about. 75%, preferably from about 45% to about 95%, water; and from about 0.1% to about 10%, preferably from about 0.5% to about 5%, of an emulsifier. Such creams would typically comprise from about 0.1% to about 20%, preferably from about 0.5% to about 10%, of the chelating agent; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

If the topical pharmaceutical/cosmetic compositions of the present invention are formulated as a gel or a cosmetic stick, a suitable amount of a thickening agent, as disclosed supra, is added to a cream or lotion formulation.

The topical pharmaceutical/cosmetic compositions of the present invention may also be formulated as makeup products such as foundations, or lipsticks.

The topical pharmaceutical/cosmetic compositions of the present invention may contain, in addition to the aforementioned components, a wide variety of additional oil-soluble materials and/or water-soluble materials conventionally used in topical compositions, at their art-established levels.

Various water-soluble materials may also be present in the compositions of this invention. These include humectants, proteins and polypeptides, preservatives and an alkaline agent. In addition, the topical compositions herein can contain conventional cosmetic adjuvants, such as dyes, opacifiers (e.g., titanium dioxide), pigments and perfumes.

The topical pharmaceutical/cosmetic compositions of the present invention may also include a safe and effective amount of a penetration enhancing agent. A safe and effective amount is generally from about 1% to about 5% of the composition. Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and European Patent Application 0043738, Cooper et al., published January 13, 1982.

Other conventional skin care product additives may also be included in the compositions of the present invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions of the present invention. For example, Vitamin A, and derivatives thereof, Vitamin $B_2$, biotin, pantothenic, Vitamin D, and mixtures thereof may be used.

A. Oral Dose Forms

Various oral dosage forms can be used, including such solid forms as tablets, capsules, granules, bulk powders and microcapsules of the drug. These oral forms comprise a safe and effective amount, usually at least about 5%, and preferably from about 25% to about 50% of the compound of the present invention. Tablets can be compressed, enteric-coated, sugar-coated or film-coated containing suitable binders, lubricants, surfactants, diluents, disintegrating agents, coloring agents, flavoring agents, preservatives, flow-inducing agents, and melting agents. Liquid oral dosage forms include aqueous and nonaqueous solutions, emulsions, suspensions, solutions and/or suspensions reconstituted from non-effervescent granules, containing suitable solvents, preservatives, emulsifying agents, suspending agents, diluents, sweeteners, melting agents, coloring agents, and flavoring agents. Preferred carriers for oral administration include gelatin and propylene glycol. Specific examples of pharmaceutically-acceptable carriers and excipients that may be used in formulating oral dosage forms containing compounds of the present invention are described in U.S. Pat. No. 3,903,297, Robert, issued Sep. 2, 1975, incorporated by reference herein. Techniques and compositions for making solid oral dosage forms are described in Marshall, "Solid Oral Dosage Forms," *Modern Pharmaceutics*, Vol. 7, (Banker and Rhodes, editors), 359–427 (1979). Techniques and compositions for making tablets (compressed, formulas and molded), capsules (hard and soft gelatin) and pills are described in Remington's Pharmaceutical Sciences (Arthur Osol, editor), 1553– 1593 (1980).

The preferred unit dosage forms for oral administration are tablets, capsules and the like, comprising a safe and effective amount of a compound of the present invention. Preferably oral dose forms comprise from about 1000 mg to about 0.1 mg of a chelating agent of the present invention, more preferably from about 500 mg to about 1 mg, and most preferably from about 100 mg to about 5 mg.

C. Injectable Dose Forms

The compounds of the present invention are also useful when injected. The dosage of the compound of the present invention which is both safe and effective to provide free radical reaction regulating activity will vary with the particular condition being treated, the severity of the condition, the duration of treatment, the specific compound employed and its usage concentration, and like factors within the specific knowledge and expertise of the attending physician and commensurate with a reasonable benefit/risk ratio associated with the use of any drug compound. The injectable dosages and dosage ranges given herein are based on delivery of the compound of the present invention to a 70 kg human and can be adjusted to provide equivalent dosages for patients of different body weights.

Methods and materials for manufacturing injectables can be found in *Remington's Pharmaceutical Sciences*, 17ed., 1985, Chapter 85, p. 1518. Materials for use in injectables are also described more fully hereinafter.

Generally, three types of injectable dosage forms are preferred: 1) aqueous solutions; 2) non-aqueous solutions; and 3) emulsions. The above dosage forms typically contain from about 0.001 mg/ml to about 10 mg/ml of a compound of the present invention, preferably from about 0.1 mg/ml to about 1 mg/ml, more preferably from about 0.4 mg/ml to about 0.6 mg/ml.

Injectable dose forms for regulating free radical reactions in the human body typically comprise from about 1000 mg to about 0.1 mg, and preferably from about 100 mg to about 1 mg, of the chelating agent of the present invention.

Cleaning Compositions

The skin cleaning compositions of the present invention comprise, in addition to the chelating agent, a cosmetically-acceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being commingled with the chelating agent in a manner such that there is no interaction which would substantially reduce the efficacy of the composition for protecting the skin from the effects of UV radiation.

The skin cleaning compositions of the present invention contain from about 0.1% to about 25%, preferably from about 0.5% to about 10%, of the chelating agent and from about 1% to about 90%, preferably from about 50% to about 85%, of a cosmetically acceptable surfactant.

The physical form of the skin cleansing compositions is not critical. The compositions can be, for example, formulated as toilet bars, liquids, pastes, or mousses. Toilet bars are most preferred since this is the form of cleansing agent most commonly used to wash the skin.

The surfactant component of the compositions of the present invention are selected from anionic, nonionic, zwitterionic, amphoteric and ampholytic surfactants, as well as mixtures of these surfactants. Such surfactants are well-known to those skilled in the detergency art.

The cleaning compositions of the present invention can optionally contain, at their art-established levels, materials which are conventionally used in skin cleansing compositions.

Combination Actives

A Sunscreens and Sunblocks

Optimum protection against sun damage can be obtained by using a combination of the non-sunscreening photoprotection agent of the present invention together with sunscreens or sunblocks. Useful sunblocks include, for example, zinc oxide and titanium dioxide.

The photoprotecting capability of the chelating agent is primarily against UVB radiation. Thus, the combination of the chelating agent with a UVA sunscreen would be most desirable. Additional UVB protection may also be included in such compositions. The inclusion of sunscreens in compositions of the present invention at low levels will not significantly reduce the tanning response of the user but will enhance immediate protection against acute UV damage.

A wide variety of conventional sunscreening agents are suitable for use in combination with the chelating agent. Segarin, et al., at Chapter VIII, pages 189 et seq., of *Cosmetics Science and Technology*, disclose numerous suitable agents. Specific suitable sunscreening agents include, for example: p-Aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropyleneglycol esters); Cinnamic acid derivatives (menthyl and benzyl esters, α-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbotol) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-di-benzoylmethane.

Of these, 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl p-dimethylamino-benzoate, 2-phenylbenzimidazole-5-sulfonic acid, 2-(p-dimethylaminophenyl)-5-sulfonicbenzoxazoic acid and mixtures of these compounds, are particularly useful.

Preferred sunscreens useful in the compositions of the present invention are 2-ethylhexyl p-methoxycinnamate, butylmethoxydibenzoylmethane, 2-hydroxy-4-methoxybenzophenone, octyldimethyl p-aminobenzoic acid and mixtures thereof.

A safe and photoprotectively effective amount of sunscreen may be used in the chelating agent compositions of the present invention. The sunscreening agent must be compatible with the chelating agent. Generally the composition may comprise from about 1% to about 20%, preferably from about 2% to about 10%, of a sunscreening agent. Exact amounts will vary depending upon the sunscreen chosen and the desired Sun Protection Factor (SPF). Because of the chelating agent's photoprotecting capability against erythema, the combination provides an SPF greater than that of the sunscreen alone.

Also particularly useful in the present invention are sunscreens such as those disclosed in Sabatelli, U.S. Pat. No. 4,937,370 and Sabatelli et al., U.S. Pat. No. 4,834,983. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)dibenzoylmethane; N-N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

The compositions of the present invention, with or without sunscreens, may also be formulated as shampoos, conditioners, mousses or other hair care products. It is known that UV radiation damages hair and the photoprotecting agents of the present invention may minimize such damage. Furthermore such formulations will provide a means for applying the photoprotecting agents of the present invention onto the scalp, which is also susceptible to UV damage. Any compatible art-recognized hair care formulations can be used with the chelating agent added at a level of from about 1% to about 5%. If desired, a sunscreen may also be included at from about 1% to about 5%.

An agent may also be added to any of the compositions of the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred photoprotection composition of the present invention, an anti-inflammatory agent is included as an active along with the chelating agent. The inclusion of an anti-inflammatory agent enhances the photoprotection benefits of the compositions. The anti-inflammatory agent protects strongly in the UVA radiation range (though it also provides some UVB protection as well), while the chelating agent protects strongly in the UVB radiation range. Thus the combination provides broad protection. The topical use of anti-inflammatory agents reduces photo-aging of the skin resulting from chronic exposure to UV radiation. (See U.S. Pat. No. 4,847,071, Bissett, Bush, and Chatterjee, issued Jul. 11, 1989; and U.S. Pat. No. 4,847,069, Bissett and Chatterjee, issued Jul. 11, 1989.) It has also been discovered that the combination of an anti-inflammatory agent and the chelating agent provides greater photoprotection than is provided by each active alone.

A safe and photoprotectively effective amount of an anti-inflammatory agent may be added to the compositions of the present invention, generally from about 0.1% to about 10%, preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflupredname, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use in the present invention is hydrocortisone.

A second class of anti-inflammatory agents which is useful in the compositions of the present invention includes the nonsteroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including *Anti-inflammatory and Anti-Rheumatic Drugs*, K. D. Rainsford, Vol. I-III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in the composition of the present invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenybutazone, oxyphenbutazone, feprazone, azapropazgne, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the present invention are the anti-inflammatory agents disclosed in U.S. Pat. No. 4,708,966, Loomans et al., issued Nov. 24, 1987. This patent discloses a class of nonsteroidal anti-inflammatory compounds which comprise specifically substituted phenyl compounds, especially substituted 2,6-di- tert-butyl phenol derivatives. For example, compounds selected from 4-(4'-pentyn-3'-one)-2,6-di-t-butylphenol; 4-(5'-hexynoyl)2,6-di-t-butylphenol; 4-((S)-(–)-3'-methyl-5'-hexynoyl)-2,6-di-t-butylphenol; 4-((R)-(+)-3'-methyl-5 '-hexynoyl)-2,6-di-t-butylphenol; and 4-(3',3'-dimethoxypropionyl)-2,6-di-t-butylphenol are useful in the present invention.

Yet another class of anti-inflammatory agents which are useful in the present invention are those disclosed in U.S. Pat. No. 4,912,248, Mueller, issued Mar. 27, 1990. This patent discloses compounds and diastereomeric mixtures of specific 2-naphthyl- containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)- naproxol-(S)-2-methyl butyrate, diasteromeric mixtures of (S)-naproxen-(S)-2-butyl ester and (S)-naproxen-(R)-2-butyl ester, and diasteromeric mixtures of (S)-naproxol-(R)-2-methyl butyrate and (S)-naproxol-(S)-2-methyl butyrate are useful in the present invention.

Finally, so-called "natural" anti-inflammatory agents are useful in the present invention. For example, candelilla wax, alpha bisabolol, aloe vera, Manjistha (extracted from plants in the genus Rubia, particularly Rubia Cordifolia), and Guggal (extracted from plants in the genus Commiphora, particularly Commiphora Mukul), may be used.

An even more preferred composition of the present invention comprises a chelating agent, a sunscreen, and an anti-inflammatory agent together for photoprotection in the amounts disclosed for each individually hereinabove.

The photoprotection compositions of the present invention may comprise, in addition to the chelating agent, a safe and photoprotectively effective amount of a radical scavenging compound, generally from about 1% to about 20%, preferably from about 2% to about 10%, more preferably from about 3% to about 5% of the composition. Examples of such radical scavenging compounds an ascorbic acid (Vitamin C) and its salts, tocopherol (Vitamin E), other tocopherol esters, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxyfumaric acid and its salts. Each of these compounds has photoprotecting capabilities. The use of the radical scavenger tocopherol sorbate in the present invention in combination with the chelating agent is preferred.

C. Anti-Oxidants/Radical Scavengers

In a preferred photoprotection composition of the present invention, an anti-oxidant/radical scavenger is included as an active along with the chelating agent. The inclusion of an anti-oxidant/radical scavenger increases the photoprotection benefits of the composition.

A safe and photoprotectively effective amount of an anti-oxidant/radical scavenger may be added to the compositions of the present invention, generally from about 0.1% to about 10%, preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used.

In a preferred photoprotection composition of the present invention, compositions comprise one, any two, or all three of a sunscreening agent, anti-inflammatory agent, and/or an antioxidant/radical scavenging agent included as actives along with the chelating agent. The inclusion of two or all three of these agents with the chelator increases the photoprotection benefits of the composition.

Methods for Regulating Biochemical Damage Caused by Free Radical Reactions in a Living Person The present invention further relates to a method for regulating biochemical or cellular damage resulting from free radical reactions in a living person. Such a method comprises administering, preferably topically, orally, or parenterally a safe and free radical regulating effective amount of the specifically defined chelating agents disclosed hereinabove to be useful in the present invention. The amount of chelating agent and frequency of application will vary widely depending upon the level of free radical reactions occurring in the subject and the level of regulation of these reactions desired.

Typically, a safe and free radical regulating effective amount in a topical composition is from about 0.001 mg to about 1.0 mg, preferably from about 0.01 mg to about 0.5 mg, more preferably from about 0.05 mg to about 0.1 mg of the chelating agent per $cm^2$ of skin. Application preferably ranges from about 1 to about 6 times daily, more preferably from about 2 to about 4 times daily. For particularly effective compositions once per day application is preferred.

A safe and free radical regulating effective amount in an orally dosed composition is from about 0.1 mg to about 1000 mg, more preferably from about 1 mg to about 500 mg, of the chelating agent per dose. Dosing would range from about I to about 6 times daily, more preferably from about 2 to about 4 times daily. For particularly effective compositions once per day dosing is preferred.

A safe and free radical regulating effective amount of a parenterally dosed composition is from about 0.1 mg to about 1000 mg, more preferably from about 1 mg to about 500 mg, of th chelating agent per dose. Dosing would range from about 1 to about 6 times daily, more preferably from about 2 to about 4 times daily. For particularly effective compositions once per day dosing is preferred.

Method For Preventing Deleterious Effects Caused by UV Exposure

The present invention further relates to a method for protecting the skin of humans and lower animals from the deleterious effects of UV radiation. Such protection by the chelating agent extends to damage resulting from acute UV exposure, e.g. erythema. It also more particularly extends to protection from damage resulting from chronic UV exposure, e.g. photoaging. Such a method comprises applying to the skin of the human or lower animal a safe and photoprotectively effective amount of the chelating agents disclosed hereinabove to be useful in the present invention. This may be accomplished by using a composition comprising the chelating agent as disclosed hereinabove. The actives involved in each of the following methods may be simply spread over the skin, or rubbed into the skin to enhance penetration of the chelating agent. The actives are applied in conjunction with UV exposure, i.e., prior to, during, or after UV exposure. More specifically, the actives may be applied several hours, preferably up to 4 hours, prior to UV exposure, up to 30 minutes after UV exposure, or anytime in between. For protection against acute damage from UV-radiation, application of the actives just prior to exposure is preferred. For protection against chronic damage from UV radiation, application is preferably 1 to 5 times daily, more preferably about 2 times daily, but for particularly effective compositions preferably once daily. Typically a safe and photoprotectively effective amount is from about 0.001 mg to about 1.0 mg, preferably from about 0.01 mg to about 0.5 rag, more preferably from about 0.05 mg to about 0.1 mg of the chelating agent per cm² skin.

A preferred method of the present invention for preventing deleterious effects caused by UV exposure involves applying both a safe and photoprotectively effective amount of a chelating agent and a safe and photoprotectively effective amount of one or more of a sunscreening agent, an anti-inflammatory agent, and/or a radical scavenging compound (as defined hereinbefore) to the skin simultaneously. By "simultaneous application" or "simultaneously" is meant applying the agents to the skin at the same situs on the body at about the same time. Though this can be accomplished by applying the agents separately to the skin, preferably a composition comprising all the desired agents commingled is applied to the skin. The amount of sunscreening agent applied is generally from about 0.01 mg to about 1.0 mg, preferably from about 0.05 mg to about 0.5 mg, per cm² of skin. The amount of radical scavenging compound applied is generally from about 0.01 mg to about 1.0 mg, preferably from about 0.05 mg to about 0.5 mg, per cm² skin. The amount of anti-inflammatory agent is generally from about 0.005 mg to about 0.5 mg, preferably from about 0.01 mg to about 0.1 mg.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE 1

A moisturizing lotion is prepared by combining the following components utilizing conventional mixing techniques.

| Components | Percent by Weight of Composition |
| --- | --- |
| Water (purified) | 70.94 |
| Carbomer viscosity control agents (commercially available in the Acritamer series from R.I.T.A. Corp.) | 0.23 |
| Alkyl Parabens | 0.90 |
| Glycerin | 3.50 |
| Potassium Hydroxide | 0.09–0.15 |
| Tetrasodium EDTA | 0.10 |
| Cetyl Alcohol | 1.25 |
| Stearic Acid | 0.75 |
| Glyceryl Stearate | 0.63 |
| Polyoxyethylene Stearyl Alcohol (commercially available in the Brij series from ICI Americas, Inc.) | 1.75 |
| Coco-Caprylate/caprate | 2.00 |
| $C_{12}$–$C_{15}$ Alcohol Benzoate (Finsolv TN - commercially available from Finetex, Inc.) | 2.00 |
| Di-(2-Furyl) Ethanedione Amphi-Dioxime | 2.00 |
| Octyl Methoxycinnamate | 7.50 |
| Benzophenone-3 | 1.00 |
| Octyl Dimethyl PABA | 1.00 |
| Dimethicone | 0.30 |
| Imidazolidinyl Urea | 0.10 |
| Ethylene Acrylate Copolymer | 3.80 |
| Tyrosine | 0.10 |

This lotion may be topically applied to inhibit damage caused by acute or chronic UV exposure. Use of an amount of lotion sufficient to deposit about 0.5 mg/cm² of di-(2-furyl) ethanedione amphi-dioxime, and about 0.5 mg/cm² of the sunscreening agents to the skin immediately prior to UV exposure is appropriate.

EXAMPLE II

A skin lotion is prepared by combining the following components utilizing conventional mixing techniques.

| Component | Percent by Weight Of Composition |
| --- | --- |
| 4-N,N-(2-Ethylhexyl)methylamino-benzoic Acid Ester of 4-(2-Hydroxyethoxy)-dibenzoylmethane | 10.00 |
| Water (purified) | 45.54 |
| Dimethyl Isosorbide | 9.00 |
| Dioctyl Maleate | 8.00 |
| $C_{12}$–$C_{15}$ Alcohol Benzoate (Finsolv TN-commercially available from Finetex, Inc.) | 8.00 |
| Glycerin | 3.50 |
| Ethylene Acrylate Copolymer | 3.80 |
| Di-(5-Methyl-2-Thienyl) Ethanedione Dioxime | 2.00 |
| Tocopherol Sorbate | 2.00 |
| Cetyl Alcohol | 1.75 |
| Polyoxyethylene Stearyl Alcohol (commercially available in the Brij series from ICI Americas, Inc.) | 1.75 |
| Stearic Acid | 1.25 |
| Glyceryl Stearate | 1.13 |
| Alkyl Parabens | 0.90 |
| Titanium Dioxide | 0.40 |
| Dimethicone | 0.30 |
| Carbomer viscosity control agents (commercially available in the Acritamer series from R.I.T.A. Corp.) | 0.23 |
| Imidazolidinyl Urea | 0.10 |
| Potassium Hydroxide | 0.15 |
| Tyrosine | 0.10 |
| Tetrasodium EDTA | 0.10 |

This lotion is useful for topical application to inhibit damage caused by acute or chronic UV exposure. Use of an amount of lotion sufficient to deposit about 0.5 mg/cm² of di-(5-methyl-2-thienyl) ethanedione dioxime, about 0.5 mg/cm² tocopherol sorbate, and about 0.5 mg/cm² of the sunscreening agents to the skin up to 4 hours prior to UV exposure is appropriate.

EXAMPLE III

A suntan cream is prepared by combining the following components utilizing conventional mixing techniques.

| Component | Percent by Weight of Composition |
| --- | --- |
| Mineral Oil | 20.00 |
| Octyl Palmitate | 10.00 |
| Glyceryl Isostearate | 4.00 |
| Octyl Methoxycinnamate | 7.50 |
| Oxybenzone | 3.00 |
| Polyethylene (AC-617-A,AC-6-A available from Allied Chemical) | 2.00 |
| Alkyl parabens | 0.30 |
| Glycerin | 2.00 |
| 4,5-Di-(2-Thienyl) Furoxan | 2.00 |
| Ibuprofen | 1.00 |
| Water (purified) | q.s. |

This cream is useful for topical application to inhibit damage caused by acute or chronic UV exposure. Use of an amount of cream sufficient to deposit about 0.5 mg/cm² of 4,5-di-(2-thienyl) furoxan, about 0.5 mg/cm$^2$ of the sunscreening agents, and about 0.1 mg/cm$^2$ of ibuprofen to the skin immediately following UV-exposure is appropriate.

EXAMPLE IV

A suntan stick is prepared by combining the following components utilizing conventional mixing techniques.

| Component | Percent by Weight of Composition |
| --- | --- |
| Candelilla Wax | 18.25 |
| Ozokerite Wax | 18.25 |
| Petrolatum | 18.25 |
| Lanolin | 15.00 |
| Mineral Oil | 14.85 |
| Octyl Dimethyl PABA | 7.00 |
| Benzophenone-3 | 3.00 |
| BHA (preservative: butylated hydroxy anisole) | 0.05 |
| Propylparaben | 0.10 |
| Di-(4-Ethyl-2-Furyl) Ethanedione Dioxime | 5.00 |
| Flavor | q.s. |

This stick is useful for topical application, for example to the lips, to inhibit damage caused by acute or chronic UV exposure. Use of an amount of stick sufficient to deposit about 1.0 mg/cm$^2$ of di-(4-ethyl-2-furyl) ethanedione dioxime, and about 0.5 mg/cm$^2$ of the sunscreening agents to the lips immediately prior to UV exposure is appropriate.

EXAMPLE V

A low SPF suntan cream is prepared by combining the following components utilizing conventional mixing techniques.

| Component | Percent by Weight of Composition |
| --- | --- |
| Tetrasodium EDTA | 0.05 |
| Alkylparabens | 0.30 |
| Carbopol (polyacrylic acid polymer-conwnercially available from B. F. Goodrich Chemical) | 0.20 |
| Glycerin | 2.00 |
| Laureth-23 (polyethylene glycol ether of lauryl alcohol) | 3.00 |
| Sorbitan Stearate | 1.50 |
| Octyl Dimethyl PABA | 3.00 |
| Dimethicone | 2.00 |
| Stearyl Alcohol | 6.00 |
| Triethanolamine | 0.20 |
| Di-(2-Thienyl) Ethanedione Amphi-Dioxime | 2.00 |
| Water (purified) | q.s. |

This cream is useful for topical application to inhibit damage caused by acute or chronic UV exposure. Use of an amount of cream sufficient to deposit about 0.5 mg/cm$^2$ of di-(2-thienyl) ethanedione amphi-dioxime, and about 0.5 mg/cm$^2$ of the sunscreening agents to the skin immediately prior to UV exposure is appropriate.

EXAMPLE VI

A suntan aqueous face gel is prepared by combining the following components utilizing conventional mixing techniques.

| Component | Percent by Weight Of Composition |
| --- | --- |
| Water (purified) | 50.00 |
| Aloe | 38.00 |
| Carbopol | 1.00 |
| Glycerin | 3.00 |
| Methylparaben | 0.20 |
| Triethanolamine | 0.90 |
| 2-Phenyl-Benzimedoic Sulfonic Acid | 2.00 |
| Octoxynol-13 (ethoxylated alkyl phenol $(C_8H_{17})(C_6H_4)(OCH_2CH_2)_nOH$, n = av. val. 13) | 1.50 |
| Di-(2-Pyrrolyl) Ethanedione Amphi-Dioxime | 2.00 |
| Color and Fragrance | q.s. |

This aqueous gel is useful for application to the face to inhibit damage caused by acute or chronic UV exposure. Use of an amount of gel to deposit about 0.5 mg/cm$^2$ of di-(2-pyrrolyl ethanedione amphi-dioxime to the face immediately prior to UV exposure is appropriate.

EXAMPLE VII

A suntan gel is prepared by combining the following components utilizing conventional mixing techniques.

| Component | Percent by Weight of Composition |
| --- | --- |
| Ozokerite Wax | 10.00 |
| Paraffin | 10.00 |
| Petrolatum | 10.00 |
| Isopropyl Myristate | 5.00 |
| Mineral Oil | 58.00 |
| Octyl Dimethyl PABA | 2.50 |
| Propylparaben | 0.10 |
| BHA | 0.05 |
| Di-(4-Ethylphenyl) Ethanedione Dioxime | 2.00 |
| Naproxen | 2.00 |
| Fragrance and Color | q.s. |

This suntan gel is useful for topical application to inhibit damage caused by acute or chronic UV exposure. Use of an amount of gel to deposit about 0.5 mcJ/cm$^2$ of di-(4-ethylphenyl) ethanedione dioxime, about 0.5 mg/cm$^2$ of the sunscreening agent, and about 0.1 mg/cm$^2$ of naproxen to the skin immediately following UV exposure is appropriate.

EXAMPLE VIII

A suntan oil is prepared by combining the following components utilizing conventional mixing techniques.

| Component | Percent by Weight of Composition |
| --- | --- |
| Sesame Oil | 5.0 |
| Cyclomethicone | 20.0 |
| Isopropyl Myristate | 5.0 |
| BHA | 0.05 |
| Sorbitan Oleate | 1.0 |

-continued

| Component | Percent by Weight of Composition |
|---|---|
| Octyl Dimethyl PABA | 1.5 |
| Propylparaben | 0.7 |
| Di-(5-Methyl-2-Furyl) Ethanedione Amphi-Dioxime | 2.00 |
| Mineral Oil | q.s. |

This suntan oil is useful for topical application to inhibit damage caused by acute or chronic UV exposure. Use of an amount of oil sufficient to deposit about 0.5 mg/cm$^2$ of di-(5-methyl-2-furyl) ethanedione amphi-dioxime, and about 0.5 mg/cm$^2$ of the sunscreening agent to the skin immediately prior to UV exposure is appropriate.

EXAMPLE IX

A moisturizing oil-in-water-in-silicone sunscreen emulsion lotion is formed from the following ingredients.

| Ingredient | Percent by Weight of Composition |
|---|---|
| Aqueous Phase: | |
| Purified Water | 58.32 |
| Pantethine, 80% aq. soln. (humectant) | 0.10 |
| Methylparaben | 0.20 |
| Carbomer viscosity control agent (commercially available in the Acritamer series from R.I.T.A. Corp.) | 0.10 |
| Glycerin | 2.50 |
| Sodim alkyl polyether sulfonate (anionic emulsifier) | 0.10 |
| Oil Phase: | |
| Heavy mineral oil | 1.75 |
| Cholesterol | 1.00 |
| Cetyl palmitate | 0.20 |
| PEG-22/Dodecyl glycol copolymer | 0.20 |
| Ethylparaben | 0.10 |
| Propylparaben | 0.15 |
| Neutralizer Base: | |
| Triethanolamine | 0.10 |
| Color & Fragrance: | |
| FD & C Red No. 4 (1% aq. soln.) | 0.03 |
| Odorant Oil | 0.30 |
| Silicone Phase: | |
| Cyclomethicone/Dimethicone copolyol (90:10) | 9.50 |
| Cyclomethicone/Dimethiconol (13:87) | 5.00 |
| Cyclomethicone | 3.00 |
| Phenyl Dimethicone | 1.00 |
| Pareth-15-3 (polyethylene glycol ester of a mixed synthetic C$_{11}$–C$_{15}$ fatty alcohol, av. 3 moles EO) | 2.00 |
| Octyl Methoxycinnamate | 7.00 |
| Benzophenone-3 | 0.50 |
| Naproxen | 2.00 |
| Di-1,5-Dimethyl-2-Pyrrolyl Ethanedione Amphi-Dioxime | 2.00 |
| C$_{12-15}$ Alcohols Benzoate | 2.85 |

In a suitably sized vessel equipped with a suitable mechanical stirrer (Tekmar Model RW-20 stirring motor, manufactured by IKA-WERK, Germany), the water, pantethine, methylparaben, glycerine and sulfonate emulsifier are heated to about 72°–75° C. and mixed. Stirring is increased until a vortex forms in the aqueous solution. The thickener, Carbomer, is slowly added to the vortex and allowed to mix until completely hydrated and the resultant gel solution is free of gelatinous particles and is uniform in composition. The temperature is maintained at about 72°–75° C. with constant agitation.

The oil phase ingredients are added to a separate suitably sized vessel and heated to about 80°–85° C. using slow mechanical stirring once the oil phase becomes molten. At this point the sunscreening agents, naproxen, and di-(1,5-dimethyl-2-pyrrolyl) ethanedione amphi-dioxime are mixed in. When molten, agitation is maintained to keep the oil phase uniform during heating.

The heated oil phase is then slowly added to the heated water phase with stirring to form the oil-in-water emulsion. After addition is complete, the mechanical stirring means is slowed to avoid unnecessary aeration of the emulsion and mixing is continued for approximately fifteen minutes at 70°–75° C. The emulsion is then cooled to about 60° C. with moderate agitation. The base, triethanolamine, is then slowly added to neutralize the acidic Carbomer 940 and the emulsion (pH 6.5) is mixed at moderate speed until uniform. The homogeneous oil-in-water emulsion is then cooled to about 45°–50° C. and the colorant and odorant oil are added followed by cooling to room temperature (about 25° C.) with continued moderate agitation.

The four silicone fluids and other silicone phase ingredients are mixed together in a separate vessel until a uniform silicone phase is attained. The oil-in-water emulsion is slowly added to the silicone phase with stirring until a homogeneous oil-in-water-in-silicone double emulsion in lotion form is attained.

This moisturizing lotion is useful for topical application to inhibit damage caused by acute or chronic UV exposure. Use of an amount of lotion sufficient to deposit about 0.5 mg/cm$^2$ of di-(1,5-dimethyl-2-pyrrolyl) ethanedione amphi-dioxime, about 0.5 mg/cm$^2$ of sunscreening agents, and about 0.1 mg/cm$^2$ of naproxen to the skin immediately following UV exposure is appropriate. This lotion may also be applied several times daily, e.g., 2 or 3 times daily, for extended periods of time, i.e., greater than one week, in amounts sufficient to deposit about 0.5 mg/cm$^2$ of di-(1,5-dimethyl-2-pyrrolyl) ethanedione amphi-dioxime, about 0.5 mg/cm$^2$ of sunscreening agents, and about 0.1 mg/cm$^2$ of naproxen to the skin to inhibit damage caused by chronic UV exposure.

EXAMPLE X

A skin conditioning toilet bar is prepared from the following ingredients.

| Component | Percent by Weight of Composition |
|---|---|
| Tallow/Coconut Soap (50/50) | 61.61 |
| Water | 10.00 |
| 2-Hydroxypropylglyceryl Ether | 4.00 |
| Sodium Coconut Glyceryl Ether Sulfonate | 8.80 |
| Coconut Fatty Acid (CnFA) | 4.00 |
| Di-(3-Ethylphenyl) Ethanedione Amphi-Dioxime | 5.00 |
| Perfume | 1.40 |
| NaCl | 1.04 |
| Na$_2$SO$_4$ | 0.34 |
| Na$_4$EDTA | 0.06 |
| TiO$_2$ | 0.20 |
| Jaguar C15 (quar hydroxy propyltrimonium | 1.00 |

-continued

| Component | Percent by Weight of Composition |
|---|---|
| chloride) | |
| Merquat 550 (poly quaternium-7) | 1.00 |
| Minors (Colorants, Preservatives, Fillers, etc.) | 1.55 |

The above composition is prepared in the following manner.

Crutching Step

About 127.6 parts of a mix containing: 29.8% water, 52.7% 50/50 tallow/coconut (T/Cn) soap, 16.7% sodium coconut glyceryl ether sulfonate paste, 3.3% coconut free fatty acid (CnFA), 3.1% 2-hydroxypropylglyceryl ether, and 0.2% NaCl are heated to ca. 150°–200° F. (65°–94° C.). About 10.0 parts of the hydrated polymer JAGUAR C-15 are mixed in. The di-(3-ethylphenyl) ethanedione amphidioxime is then added and mixed in.

Vacuum Drying Step

The crutcher mix is vacuum dried at ca. 50 mm Hg absolute pressure to reduce the moisture content of the mix to ca. 10% and to plod this soap into noodles. These noodles are passed through a milling step once.

Amalgamating Step

The once-milled soap noodles are weighed and placed in a batch amalgamator. To about 99.1 parts noodles in the amalgamator are added: 0.20 part $TiO_2$, 1.4 parts perfume, 0.15 part colorant solution, 0.15 part of a solution which contains ca. 40% EDTA. The combined ingredients are mixed thoroughly.

Milling Step

Three-roll soap mills are set up with all rolls at 85–105° F (29°–41° C.). The mixture from the amalgamator is passed through the mills several times to obtain a homogeneous mix. This is an intimate mixing step. Plodding and Stamping Steps A conventional plodder is set up with the barrel temperature at about 90° F. (32° C.) and the nose temperature at about 110° F. (43° C.). The plodder used is a dual stage twin screw plodder that allows for a vacuum of about 40 to 65 mm Hg between the two stages. The soap log extruded from the plodder is typically round or oblong in cross-section, and is cut into individual plugs. These plugs are then stamped on a conventional soap stamping apparatus to yield the finished toilet soap bar.

The use of this toilet bar for cleansing provides a useful means for deposition of di-(3-ethylphenyl) ethanedione amphidioxime to the skin to inhibit damage caused by acute or chronic UV exposure. Use of the toilet bar such that about 0.05 mg/cm² of di-(3-ethylphenyl) ethanedione amphi-dioxime is deposited on the skin up to 4 hours prior to UV exposure is appropriate.

EXAMPLE XI

Facial Cleanser

A facial cleanser (lathering mousse composition) is prepared from the following ingredients.

| Emulsion Concentrate (A) | Percent by Weight of Composition |
|---|---|
| DRO Water[1] | 52.63 |
| 2-Hydroxypropyglyceryl Ether | 15.00 |
| Sodium Glyceryl Ether Sulfonate (90% Coconut/10 Tallow)-50% Active | 12.06 |
| Sodium Lauroyl Sarcosinate - 33% Active | 6.66 |
| PEG 600 | 4.00 |
| Aloe Vera Gel | 1.00 |
| Lexein LP170P (hydrolyzed animal protein) | 1.00 |
| Stearic Acid | 1.00 |
| Citric Acid | 0.30 |
| 4,5-Di-(2-Furyl) Furoxan | 5.00 |
| Jaguar C14-S (guar hydroxypropyl-trimonium chloride) | 0.25 |
| Perfume | 0.20 |
| FD & C Red Dye #4 | 0.20 |
| Lauryl Alcohol | 0.20 |
| Alkyl Parabens | 0.30 |
| Germall 115 (Imidazolidinyl urea) | 0.10 |
| $Na_4EDTA$ | 0.10 |

[1]Water purified by double reverse osmosis

A-46 Propellant (Isobutane-Propane) (B)

(6.4 g in 100 g concentrate)

The composition is prepared in a single batch process. DRO water is brought to 71.1° C. and the Jaguar polymer is added with agitation. Maintaining agitation, the following ingredients are added sequentially: Sodium glycerol ether sulfonate, Sodium lauroyl sarcosinate, lauryl alcohol, PEG-600, Parabens, EDTA, dye, 2-Hydroxypropylglyceryl ether, stearic acid, Aloe Vera Gel, citric acid and 4,5-di-(2-furyl) furoxan. The mixture is then cooled to 135°–140° F. and the following ingredients are added sequentially with stirring: Lexein, Germall and perfume. The resulting mixture is cooled to room temperature.

Aluminum cans are then filled with the cooled emulsion concentrate. Aerosol activator assemblies are then crimped onto the cans to form a tight seal. Pressurized A-46 Propellant is then pumped into the cans in an amount sufficient to provide a composition consisting of 6% propellant and 94% emulsion concentrate in each can.

Upon activation of the aerosol assembly, the composition is dispensed under pressure in the form of a creamy, foaming mousse which can be applied to the skin for cleansing and as a means for deposition of 4,5-di-(2-furyl) furoxan to the skin to inhibit damage caused by acute or chronic UV exposure. Use of amount of facial cleanser sufficient to deposit about 0.05 mg/cm² of 4,5-di-(2-furyl) furoxan to the skin up to 4 hours prior to UV exposure is appropriate.

EXAMPLE XII

A cream soap is prepared by combining the following ingredients as described below.

| Component | Percent by Weight of Composition |
|---|---|
| Sodium Lauroyl Glutamate (Acylglutamate LS-11) (28) | 22.00 |

-continued

| Component | Percent by Weight of Composition |
| --- | --- |
| Sodium Hydrogenated Tallow Glutamate and Cocoyl Glutamate (Acylglutamate GS-11) (28) | 3.00 |
| Polyethylene Glycol 400 | 10.00 |
| Polyethylene Glycol (M.W. 6300) Monostearate | 5.00 |
| Polyoxyethylene (20) Sorbitan Monostearate | 3.00 |
| Di-5-Methyl-2-Pyrrolyl Ethanedione Amphi-Dioxime | 3.00 |
| Tocopherol Sorbate | 5.00 |
| Flufenamic Acid | 2.00 |
| 2-Ethylhexyl Methoxycinnamate | 3.00 |
| Water | 30.50 |
| Glycerin | 10.00 |
| Fragrance and Preservative | q.s. |

The sodium glutamate, sodium hydrogenated tallow glutamate and cocoyl glutamate, polyethylene glycol, polyethylene glycol monostearate, polyoxyethylene sorbitan monostearate, di-5-methyl-2-thienyl ethanedione amphi-dioxime, tocopherol sorbate, flufenamic acid, 2-ethylhexyl methoxycinnamate, and water are dissolved together with heating. The glycerin is added with agitation. The mixture is cooled to about 60° C. and the fragrance and preservative are added. The mixture is cooled to 35° C. with agitation.

The result is a cream soap the use of which for cleansing provides a useful means for deposition of di-(5-methyl-2-pyrrolyl) ethanedione amphi-dioxime, tocopherol sorbate, flufenamic acid, and 2-ethylhexyl methoxycinnamate to the skin to inhibit damage caused by acute or chronic UV exposure. Use of an amount of cream soap sufficient to deposit about 0.05 mg/cm² of di-(5-methyl-2-pyrrolyl) ethanedione amphi-dioxime, 0.05 mg/cm² of tocopherol sorbate, 0.05 mg/cm² of the sunscreening agent, and 0.01 mg/cm² of flufenamic acid to the skin prior to or immediately following UV exposure is appropriate.

EXAMPLE XIII

A shampoo composition is made by combining the following components.

| Component | Percent by Weight of Composition |
| --- | --- |
| Ammonium Lauryl Sulfate | 12.0 |
| Ammonium Xylene Sulfonate | 2.2 |
| Ammonium Laureth Sulfate | 4.0 |
| NaCl | 0.5 |
| Di-1-(Methyl-5-Ethyl-2-Pyrrolyl) Ethanedione Amphi-Dioxime | 5.0 |
| Octyl Dimethyl PABA | 7.0 |
| Water | 68.1 |
| Perfume and Minor Ingredients | 1.2 |

The ammonium lauryl sulfate, ammonium laureth sulfate, and ammonium xylene sulfonate are first mixed together. The di-(1-methyl-5-ethyl-2-pyrrolyl) ethanedione amphi-dioxime and octyl dimethyl PABA and perfume and minor ingredients are added and the resulting mixture is agitated in a Teckmar® Mill set at 70 for 2 minutes at 70° C.

The resulting shampoo composition is added to hair which has been wetted with water, worked through the hair then rinsed out. This allows for deposition of di-(1-methyl-5-ethyl-2-pyrrolyl) ethanedione amphi-dioxime and octyl dimethyl PABA to the scalp to inhibit damage caused by acute or chronic UV exposure. Use of an amount of shampoo sufficient to deposit about 0.05 mg/cm² of di-(1-methyl-5-ethyl-2-pyrrolyl ) ethanedione amphi-dioxime and 0.05 mg/cm² of sunscreening agent to the scalp prior to or immediately following UV exposure is appropriate.

What is claimed is:

1. A topical composition comprising:
   (a) a safe and effective amount of one or more α-diamine compounds having the structure:

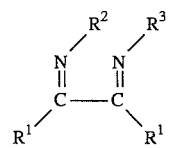

wherein each —$R^1$ is independently selected from the group consisting of alkyl, aryl, heteroaryl and heterocyclic, or the —$R^1$'s are covalently bonded together to form a cyclic alkyl ring; each heteroaryl, if any, being independently selected from the group consisting of furyl, thienyl, pyrrolyl, imidazolyl, pyrazolyl, pyrazinyl, pyrimidinyl, pyridazinyl, isoquinolyl, purinyl, phthalazinyl, quinoxalinyl, furazanyl, isoxazolyl, and tetrazolyl; each heterocyclic ring, if any, being independently selected from the group consisting of the saturated analogs of the above listed group of heteroaryl rings;

—$R^2$ and —$R^3$ are —$OR^4$ in which case there is no bond or polar bond between —$R^2$ and the nitrogen covalently bonded to —$R^3$, each —$R^4$ being independently selected from the group consisting of hydrogen, alkyl and aryl, except that both —$R^4$'s are not methyl when both —$R^1$'s are furyl; or —$R^2$— is —O— and is covalently bonded to the nitrogen which is covalently bonded to —$R^3$, and —$R^3$ is —O— there being a + charge on the nitrogen to which it is bonded) or nil;

wherein the α-diamine compounds consist essentially of compounds wherein =$NR^2$ and =$NR^3$ are in amphi configuration when both —$R^2$ and —$R^3$ are —OH, and when both —$R^1$'s are furyl or the —$R^1$'s are covalently bonded together to form a cyclohexanedione structure; and (b) a pharmaceutically-acceptable topical carrier.

2. The composition of claim 1 wherein the α-diamine compound exhibits at least 20% decrease in Ornithine Decarboxylate Value relative to the Ornithine Decarboxylase Value of a control in the Standard Method Assay of Ornithine Decarboxylase.

3. The composition of claim 2 wherein each —$R^1$ is independently selected from aryl or heteroaryl selected from the group consisting of phenyl, naphthyl, furyl, thienyl, pyrrolyl, imidazolyl, pyrazolyl, pyrazinyl, pyrimidinyl, pyridazinyl, isoquinolyl, purinyl, phthalazinyl, quinoxalinyl, furazanyl, isoxazolyl, and tetrazolyl, wherein any aryl or heteroaryl substituent is selected from hydroxy and $C_1$-$C_4$ alkyl; and wherein both —$R^4$'s are hydrogen.

4. The composition of claim 3 wherein the α-diamine compounds consist essentially of compounds wherein =$NR^2$ and =$NR^3$ are in amphi configuration.

5. The composition of claim 3 wherein —$R^2$— is —O— and —$R^3$ is nil, and wherein the two —$R^1$'s are the same.

6. The composition of claim 3 wherein —$R^2$— is —O— and —$R^3$ is nil, and wherein the two —$R^1$'s are the same.

7. The composition of either claim 5 or 6 wherein the two —$R^1$'s are selected from the group consisting of unsubstituted or substituted phenyl, furyl, thienyl, and pyrrolyl.

8. A topical composition comprising:
   (a) a safe and effective amount of one or more α-diamine compounds having the structure:

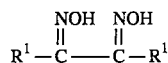

wherein each —$R^1$ is independently selected from the group consisting of alkyl, aryl, heteroaryl and heterocyclic or the —$R^1$'s are covalently bonded together to form a cyclic alkyl ring; each heteroaryl, if any, being selected from the group consisting of furyl, thienyl, pyrrolyl, imidazolyl, pyrazolyl, pyrazinyl, pyrimidinyl, pyridazinyl, isoquinolyl, purinyl, phthalazinyl, quinoxalinyl, furazanyl, isoxazolyl and tetrazolyl; each heterocyclic ring, if any, being independently selected from the group consisting of the saturated analogs of the above listed group of heteroaryl rings;

wherein the α-diamine compounds consist essentially of compounds wherein the two =NOH's are in amphi configuration when both —$R^1$'s are furyl or the —$R^1$'s are covalently bonded to form a cyclohexanedione structure;

the α-diamine compounds exhibiting at least 20% decrease in Ornithine Decarboxylase Value relative to the Ornithine Decarboxylase Value of a control in tie Standard Method Assay of Ornithine Decarboxylase; and (b) a pharmaceutically-acceptable topical carrier.

9. The composition of claim 8 wherein each —$R^1$ is aryl or heteroaryl independently selected from the group consisting of phenyl, naphthyl, furyl, thienyl, pyrrolyl, imidazolyl, pyrazolyl, pyrazinyl, pyrimidinyl, pyridazinyl, isoquinolyl, purinyl, phthalazinyl, quinoxalinyl, furazanyl, isoxazolyl, and tetrazolyl.

10. The composition of claim 9 wherein each —$R^1$ is heteroaryl, unsubstituted or mono- or disubstituted with $C_1$–$C_4$ alkyl.

11. The composition of claim 10 wherein both $R_1$'s are the same.

12. The composition of claim 9 wherein the —$R^1$ are selected from the group consisting of furyl, thienyl and pyrrolyl, unsubstituted or monosubstituted with $C_1$–$C_4$ alkyl.

13. The composition of claim 12 wherein both —$R^1$'s are the same.

14. The composition of any of claims 10–13 wherein the α-diamine compounds consist essentially of compounds wherein the two =NOH's are in amphi-configuration.

15. A method of protecting against photodamage of the skin comprising administering to the skin of a human a topical photoprotective composition of any of claims 2, 5, 6, 8, 10, 11, 12 and 13.

16. A method of protecting against photo damage of the skin comprising administering to the skin of a human a composition comprising:

(a) a safe and effective amount of one or more α-diamine compounds having the structure

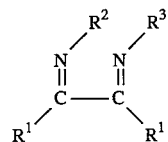

wherein each —$R^1$ is independently selected from the group consisting of alkyl, aryl, heteroaryl and heterocyclic, or the $R^1$'s are covalently bonded together to form a cyclic alkyl ring; each heteroaryl, if any, being independently selected from the group consisting of furyl, thienyl, pyrrolyl, imidazolyl, pyrazolyl, pyrazinyl, pyrimidinyl, pyridazinyl, isoquinolyl, purinyl, phthalazinyl, quinoxalinyl, furazanyl, isoxazolyl, and tetrazolyl; each heterocyclic ring, if any, being independently selected from the group consisting of the saturated analogs of the above listed group of heteroaryl rings;

—$R^2$ and —$R^3$ are —$OR^4$ in which case tiers is no bond or polar bond between —$R^2$ and the nitrogen covalently bonded to —$R^3$, each —$R^4$ being independently selected from the group consisting of hydrogen, alkyl and aryl, except that both —$R^4$'s are not methyl when both —$R^1$'s are furyl; or —$R^2$— is —O— and is covalently bonded to the nitrogen which is covalently bonded to —$R^3$, and —$R^3$ is —O— (there being a + charge on the nitrogen to which it is bonded) or nil; wherein the α-diamine compounds consist essentially of compounds wherein =$NR^2$ and =$NR^3$ are in amphi configuration when both —$R^2$ and —$R^3$ are —OH, and when both —$R^1$'s are furyl or the —$R^1$'s are covalently bonded together to form a cyclohexanedione structure; and (b) a pharmaceutically-acceptable carrier.

* * * * *

UNITED STATES PATENT AND TRADEMARK OFFICE
CERTIFICATE OF CORRECTION

PATENT NO. : 5,462,963

DATED : October 31, 1995

INVENTOR(S) : Rodney D. Bush, Donald L. Bissett

It is certified that error appears in the above-identified patent and that said Letters Patent is hereby corrected as shown below:

Column 38, line 40 (claim 1) "there" should read --(there--.
Column 39, line 1 (claim 6) "nil" should read -- 0 --.
Column 39, line 30, (claim 8) "tie" should read --the--.
Column 40, line 34, (claim 16) "tiers" should read --there--.

Signed and Sealed this

First Day of July, 1997

Attest:

BRUCE LEHMAN

*Attesting Officer*    *Commissioner of Patents and Trademarks*